US010465182B2

(12) United States Patent
Ho

(10) Patent No.: US 10,465,182 B2
(45) Date of Patent: Nov. 5, 2019

(54) COMPOSITIONS AND METHODS FOR DNA AND RNA EXTRACTION FROM TISSUE SAMPLES

(71) Applicant: Cepheid, Sunnyvale, CA (US)

(72) Inventor: Kenneth E. Ho, Sunnyvale, CA (US)

(73) Assignee: CEPHEID, Sunnyvale, CA (US)

( * ) Notice: Subject to any disclaimer, the term of this patent is extended or adjusted under 35 U.S.C. 154(b) by 44 days.

(21) Appl. No.: 15/208,525

(22) Filed: Jul. 12, 2016

(65) Prior Publication Data

US 2017/0022493 A1    Jan. 26, 2017

Related U.S. Application Data

(60) Provisional application No. 62/196,774, filed on Jul. 24, 2015.

(51) Int. Cl.
| | | |
|---|---|---|
| C12N 15/10 | (2006.01) | |
| C12Q 1/6876 | (2018.01) | |
| C12N 1/06 | (2006.01) | |
| C12Q 1/6806 | (2018.01) | |
| C12Q 1/686 | (2018.01) | |

(52) U.S. Cl.
CPC ........... *C12N 15/1003* (2013.01); *C12N 1/06* (2013.01); *C12Q 1/6806* (2013.01); *C12Q 1/686* (2013.01); *C12Q 1/6876* (2013.01); *C12Q 2600/158* (2013.01)

(58) Field of Classification Search
CPC .................................................. C12N 15/1003
USPC ....................................................... 536/25.41
See application file for complete search history.

(56) References Cited

U.S. PATENT DOCUMENTS

| | | | |
|---|---|---|---|
| 6,423,488 B1 | 7/2002 | Harvey | |
| 6,469,159 B1 | 10/2002 | Belly et al. | |
| 10,233,440 B2 | 3/2019 | Lai et al. | |
| 2002/0009794 A1 | 1/2002 | Danenberg et al. | |
| 2005/0042656 A1 | 2/2005 | Davis et al. | |
| 2006/0199197 A1 | 9/2006 | Danenberg et al. | |
| 2008/0050746 A1 | 2/2008 | McMaster et al. | |
| 2009/0047724 A1* | 2/2009 | Hillebrand | C12N 15/1003 435/219 |
| 2010/0063268 A1* | 3/2010 | Kanehara | C12N 15/1006 536/55.3 |
| 2011/0244468 A1 | 10/2011 | Hollander et al. | |
| 2013/0338350 A1 | 12/2013 | Hurt et al. | |
| 2015/0252354 A1 | 9/2015 | Lai et al. | |
| 2016/0047821 A1* | 2/2016 | Baud | G01N 33/57484 424/134.1 |

FOREIGN PATENT DOCUMENTS

| | | | |
|---|---|---|---|
| EP | 2267127 A1 | 12/2010 | |
| WO | WO 2008/035991 A2 | 3/2008 | |
| WO | WO 2009/127350 A1 | 10/2009 | |
| WO | WO 2011/104027 A1 | 9/2011 | |
| WO | WO 2011/157683 A1 | 12/2011 | |
| WO | WO 2014/052551 A1 | 4/2014 | |
| WO | WO 2017/019293 A1 | 2/2017 | |

OTHER PUBLICATIONS

Stratagene Catalog p. 39 (Year: 1988).*
U.S. Office Action dated Sep. 20, 2017 issued in U.S. Appl. No. 14/431,243.
PCT International Search Report and Written Opinion dated Dec. 26, 2013 issued in PCT/US2013/061863.
PCT International Preliminary Report on Patentability dated Mar. 31, 2015 issued in PCT/US2013/061863.
PCT International Search Report and Written Opinion dated Dec. 4, 2013 issued in PCT/US2013/061654.
PCT International Search Report and Written Opinion dated Sep. 27, 2016 issued in PCT/US2016/041917.
PCT International Preliminary Report on Patentability dated Feb. 8, 2018 issued in PCT/US2016/041917.
EP Extended Search Report dated Apr. 11, 2016 issued in EP 13842384.3.
EP Office Action dated May 12, 2017 issued in EP 13842384.3.
Alvarez-Aldana, et al. (Feb. 2015) "Comparison of five protocols to extract DNA from paraffin-embedded tissues for the detection of human papillomavirus", *Pathology Research and Practice*, 211(2): 150-155.
Anonymous, (Apr. 22, 2015) "Solution FP7 Safety Data Sheet", *Mo Bio Laboratories Inc.*, 5 pages, XP055261385, Retrieved from the Internet: URL: https://mobio.com/media/wysiwyg/pdfs/sds/12250-7.pdf [retrieved on Mar. 30, 2016].
Anonymous, (Apr. 22, 2015) "Solution FP8 Safety Data Sheet", *Mo Bio Laboratories Inc.*, 5 pages, XP055261388, Retrieved from the Internet: URL: https://mobio.com/media/wysiwyg/pdfs/sds/12250-8.pdf [retrieved on Mar. 30, 2016].
Anonymous, (Apr. 27, 2015) "Solution FP1 Safety Data Sheet", *Mo Bio Laboratories Inc.*, 5 pages, XP055261376, Retrieved from the Internet: URL: https://mobio.com/media/wysiwyg/pdfs/sds/12250-1.pdf [retrieved on Mar. 30, 2016].
Anonymous, (Apr. 28, 2009) "Bi0stic(TM) FFPE Tissue DNA Isolation Kit", *Mo Bio Laboratories Inc.*, 16 pages, XP055261373, Retrieved from the Internet: URL: http://www.biotechniques.com/multimedia/archive/00074/MO_BIO-FP-FFPE_74612a.pdf [retrieved on Mar. 30, 2016].

(Continued)

*Primary Examiner* — Jezia Riley
(74) *Attorney, Agent, or Firm* — Emily M. Haliday; Weaver Austin Villeneuve & Sampson LLP

(57) ABSTRACT

Methods and reagents are provided for the rapid extraction of nucleic acids from a cell or tissue sample. In certain embodiments the sample comprises a formalin fixed paraffin embedded sample (e.g., a FFPET sample), or a fine needle aspirate and/or a cell/tissue smear. In some embodiments, the methods comprise incubating one or more sections of said tissue sample in a lysis solution comprising a buffer sufficient to maintain the pH of said solution at a pH ranging from about pH 4 to about pH 9; a chaotropic agent; a chelating agent; and a detergent; where the incubating is at a temperature ranging from about 50° C. to about 100° C.; and recovering the nucleic acid from said lysis solution.

28 Claims, 5 Drawing Sheets

(56) References Cited

OTHER PUBLICATIONS

Anonymous, (Apr. 3, 2015) "Solution FP5 Safety Data Sheet", *Mo Bio Laboratories Inc.*, 5 pages, XP055261382, Retrieved from the Internet: URL: https://mobio.com/media/wysiwyg/pdfs/sds/12250-5.pdf [retrieved on Mar. 30, 2016].
Anonymous, (Apr. 9, 2015) "Solution FP4 Safety Data Sheet", *Mo Bio Laboratories Inc.*, 5 pages, XP055261380, Retrieved from the Internet: URL: https://mobio.com/media/wysiwyg/pdfs/sds/12250-4.pdf [retrieved on Mar. 30, 2016].
Anonymous, (Apr. 9, 2015) "Solution FP6 Safety Data Sheet", *Mo Bio Laboratories Inc.*, 5 pages, XP055261384, Retrieved from the Internet: URL: https://mobio.com/media/wysiwyg/pdfs/sds/12250-6.pdf [retrieved on Mar. 30, 2016].
Anonymous, (May 8, 2015) "Solution FP3 Safety Data Sheet", *Mo Bio Laboratories Inc.*, 5 pages, XP055261381, Retrieved from the Internet: URL: https://mobio.com/media/wysiwyg/pdfs/sds/12250-3.pdf [retrieved on Mar. 30, 2016].
Anoymous, (Apr. 27, 2015) "Solution FP2 Safety Data Sheet", *Mo Bio Laboratories Inc.*, 5 pages, XP055261377, Retrieved from the Internet: URL: https://mobio.com/media/wysiwyg/pdfs/sds/12250-2.pdf [retrieved on Mar. 30, 2016].
Bohmann, et al. (Sep. 2009) "RNA extraction from archival formalin-fixed paraffin-embedded tissue: A comparison of manual, semiautomated, and fully automated purification methods" *Clinical Chemistry*, 55(9): 1719-1727.
Butkus, (Sep. 27, 2012) "Cepheid Plans 1,000-Target PCR, Protein Detection, FFPE Analysis, Other Upgrades to GeneXpert", 6 pages, XP055261180. Retrieved from the Internet: URL: https://www.genomeweb.com/pcrsample-prepjcepheid-plans-1000-target-pcr-protein-detection-ffpe-analysis-other-upgrades-gen [retrieved on Mar. 29, 2016].
Dedhia, et al. (2007) "Evaluation of DNA extraction methods and real time PCR optimization formalin-fixed paraffin-embedded tissues" *Asian Pacific Journal of Cancer Prevention*, 8(1): 55-59.
Gilbert, et al. (Jun. 2007) "The Isolation of Nucleic Acids from Fixed, Paraffin-Embedded Tissues—Which Methods Are Useful When?" *PLOS one*, 2(6): e537 (12 pages).
Gouveia, et al. (Jan. 2014) "Comparison of Two Methods of RNA Extraction from Formalin-Fixed Paraffin-Embedded Tissue Specimens", *BioMed Research International*, 47(5): 541-5.
Hennig, et al. (Oct. 14, 2010) "Automated Extraction of DNA and RNA from a Single Formalin-Fixed Paraffin-Embedded Tissue Section for Analysis of Both Single-Nucleotide Polymorphisms and mRNA Expression." *Clinical Chemistry*, 56(12): 1845-1853.
Kennedy, Suzanne (Nov. 2009) "Isolation of DNA from FFPE samples without paraffin removal", *BioTechniques*, 3 pages; XP055261394, Retrieved from the Internet: URL: http://www.biotechniques.com/protocols/DNA_RNA_Isolation_and_Purificat/From_FFPE_Archival_Tissues/lsolation-of-DNA-from-FFPE-samples-without-paraffin-removal/biotechniques-181192.html [retrieved on Mar. 30, 2016].
Oberli, et al. (Apr. 19, 2008) "Expression profiling with RNA from formalin-fixed, paraffin-embedded material" *BMC Medical Genomics*, 1(1): 9 (15 pages).
Park, et al. (Nov. 1996) "Detection of Hepatitis C Virus RNA using Ligation-Dependent Polymerase Chain Reaction in Formalin-Fixed, Paraffin-Embedded Liver Tissues", *American Journal of Pathology*, 149(5): 1485-1491.
Shi, et al. (2004) "DNA extraction from archival formalin-fixed, paraffin-embedded tissues: heat-induced retrieval in alkaline solution", *Histochem Cell Biol*, 122:211-218.
Tang, et al. (2009) "DNA Extraction from Formalin-Fixed, Paraffin-Embedded Tissue" *Cold Spring Harb Protoc*, 4(2) (5 pages) doi: 10.1101/pdb.prot5138.
Weiss, et al. (2011) "Efficient and Cost-Effective Extraction of Genomic DNA From Formalin-Fixed and Paraffin-Embedded tissues" *Veterinary Pathology Online*, 4(4) :834-838.
U.S. Final Office Action dated Apr. 6, 2018 issued in U.S. Appl. No. 14/431,243.
U.S. Office Action [Advisory Action] dated Aug. 10, 2018 issued in U.S. Appl. No. 14/431,243.
Australian Examination report No. 1 dated Jul. 10, 2018 issued in AU 2013323586.
EP Office Action dated Jun. 22, 2018 issued in EP 13842384.3.
Thermo Fisher Scientific—AU (Nov. 19, 2011) "RNA Stabilization and Storage—RNAlater®", Thermo Fisher Scientific—AU [Retrieved from internet on Sep. 29, 2011] Viewed on internet. <URL: https://www.thermofisher.com/au/en/home/brands/product-brand/rnalater.html> published on Nov. 19, 2011 as per Wayback Machine. 4 pages.
Qiagen (Feb. 8, 2008) "FAQ—What is the recommended solution in which to store RNA samples that will be used as templates for cDNA synthesis?" (FAQ ID-2659) [Retrieved from internet on Sep. 29, 2011] Viewed on internet. <URL: https://www.qiagen.com/au/resources/faq?id=7402936b-e4d7-417c-a338-5dd555e26f82&lang=en >. Published on Feb. 8, 2008 as per Wayback Machine.
U.S. Notice of Allowance dated Oct. 23, 2018 issued in U.S. Appl. No. 14/431,243.
U.S. Notice of Allowance [Supplemental] dated Dec. 3, 2018 issued in U.S. Appl. No. 14/431,243.
EP Office Action dated Jan. 30, 2019 issued in EP 16742522.2.

\* cited by examiner

COMPOSITIONS AND METHODS FOR DNA AND RNA EXTRACTION FROM TISSUE SAMPLES

CROSS-REFERENCE TO RELATED APPLICATIONS

This application claims benefit of and priority to U.S. Ser. No. 62/196,774, filed on Jul. 24, 2015, which is incorporated herein by reference in its entirety for all purposes.

STATEMENT OF GOVERNMENTAL SUPPORT

[Not Applicable]

BACKGROUND

The use of gene expression profiling is not only prevalent in various research applications, but is rapidly becoming part of many therapeutic regimes. For example, the determination of gene expression levels in tissues is of great importance for accurately diagnosing human disease and is increasingly used to determine a patient's course of treatment. Pharmacogenomic methods can identify patients likely to respond to a particular drug and can lead the way to new therapeutic approaches For example, thymidylate synthase (TS) is an integral enzyme in DNA biosynthesis where it catalyzes the reductive methylation of deoxyuridine monophosphate (dUMP) to deoxythymidine monophosphate (dTMP) and provides a route for de novo synthesis of pyrimidine nucleotides within the cell (Johnston et al. (1995) *Cancer Res.*, 55: 1407-1412). Thymidylate synthase is a target for chemotherapeutic drugs, most commonly the antifolate agent 5-fluorouracil (5-FU). As an effective agent for the treatment of colon, head and neck and breast cancers, it is believed the primary action of 5-FU is to inhibit TS activity, resulting in depletion of intracellular thymine levels and subsequently leading to cell death.

Thymidylate synthase is also known to have clinical importance in the development of tumor resistance, as demonstrated by studies that have shown acute induction of TS protein and an increase in TS enzyme levels in neoplastic cells after exposure to 5-FU (Spears et al. (1982) *Cancer Res.* 42: 450-456; Swain et al. (1989) *J. Clin. Oncol.* 7: 890-899). The ability of a tumor to acutely overexpress TS in response to cytotoxic agents such as 5-FU may play a role in the development of fluorouracil resistance. the levels of TS protein appear to directly correlate with the effectiveness of 5-FU therapy, that there is a direct correlation between protein and RNA expression and TS expression is a powerful prognostic marker in colorectal and breast cancer (Jackman et al. (1985) *Experimental and Clinical Progress in Cancer Chemotherapy*, F. M. Muggia ed., Martinus et al. (1992) *Cancer Res.*, 52: 108-116). In advanced metastatic disease, both high TS mRNA, quantified by RT-PCR, and high TS protein expression, have been shown to predict a poor response to fluoropyrimidine-based therapy for colorectal (Johnston et al. (1995) supra.; Farrugia et al. (1997) *Proc. Annu. Meet Am. Assoc. Cancer Res.* 38: A4132; Leichman et al. (1997) *J. Clin. Oncol.* 15(10): 3223-3229), gastric (Lenz et al. (1998) *Clin. Cancer Res.*, 4(5): 1227-1234), and head and neck (Johnston et al. (1995) *Cancer Res.*, 55: 1407-1412; Leichman et al. (1997)*J. Clin. Oncol.* 15(10): 3223-3229) cancers.

Similarly, mutation of the KRAS oncogene is predictive of a very poor response to panitumumab (VECTIBIX®) and cetuximab (ERBITUX®) therapy in colorectal cancer (Lièvre et al. (2006) *Cancer Res.*, 66(8): 3992-3995). Currently, one of the most reliable ways to predict whether a colorectal cancer patient will respond to one of the EGFR-inhibiting drugs is to test for certain "activating" mutations in the gene that encodes KRAS, which occur in 40% of colorectal cancers. Studies show patients whose tumors express the mutated version of the KRAS gene will not respond to cetuximab or panitumumab.

One important source for this type of information comes in the form of formalin-fixed, paraffin-embedded tissue ("FFPET") samples, that are routinely created from biopsy specimens taken from patients undergoing a variety of diagnostic and/or therapeutic regimens for a variety of different diseases. These samples are usually associated with the corresponding clinical records and often play an important role in diagnosis and determination of treatment modality. For example, tumor biopsy FFPET samples are often linked with cancer stage classification, patient survival, and treatment regime, thereby providing a potential wealth of information that can be cross-referenced and correlated with gene expression patterns. However, the poor quality and quantity of nucleic acids isolated from FFPET samples has led to their underutilization in gene expression profiling studies.

It is known that RNA can be purified and analyzed from FFPET samples (Rupp and Locker (1988) *Biotechniques* 6: 56-60), however, RNA isolated from FFPET samples is often moderately to highly degraded and fragmented. In addition to being degraded and fragmented, chemical modification of RNA by formalin restricts the binding of oligo-dT primers to the polyadenylic acid tail and can impede the efficiency of reverse transcription.

In view of these difficulties, the analysis of nucleic acids from formalin fixed, paraffin embedded tissue (FFPET) has proven challenging due to the multiple steps required for generating PCR-amplifiable genetic material. The procedure to isolate nucleic acids from FFPET may include removal of paraffin (deparaffinization), lysis of preserved sample (protease digestion), reversal of cross-links acquired during the fixation process and solid phase-based purification of nucleic acids. These protocols are typically complex and labor intensive.

SUMMARY

Methods and reagents for the isolation of nucleic acids from cell or tissue samples (e.g., fine needle aspirates and/or fixed embedded tissue samples (e.g., FFPET samples, and/or cryosections) are provided. In some embodiments, the methods are simple, easily semi-automated or fully automated and typically require minimal hands-on time, while extracting nucleic acids of high yield and PCR-amplifiable quality.

Various embodiments contemplated herein may include, but need not be limited to, one or more of the following:

Embodiment 1

A lysis solution for the extraction of a nucleic acid from a cell or tissue sample, said lysis solution comprising: $NaCl_2$ at a concentration of greater than about 300 mM; a buffer sufficient to maintain the pH of said solution at a pH ranging from about pH 6.8 to about pH 7.3; a chelating agent; MgCl$_2$ at a concentration less than about 50 mM; and a detergent.

Embodiment 2

The lysis solution of embodiment 1, wherein said lysis solution is for a formalin fixed paraffin-embedded tissue sample.

Embodiment 3

The lysis solution of embodiment 1, wherein said lysis solution is for a fine needle aspirate and/or a cell smear.

Embodiment 4

The lysis solution according to any one of embodiments 1-3, wherein said solution comprises an antifoaming agent.

Embodiment 5

The lysis solution according to any one of embodiments 1-4, wherein said solution comprises a preservative/biocide.

Embodiment 6

The lysis solution according to any one of embodiments 1-5, wherein said buffer is a HEPES sodium salt buffer.

Embodiment 7

The lysis solution according to any one of embodiments 1-6, wherein the concentration of said buffer ranges from about 10 mM up to about 100 mM, or from about 20 mM up to about 50 mM, or is about 50 mM.

Embodiment 8

The lysis solution according to any one of embodiments 1-7, wherein the pH of said solution ranges from about 6.8 to about 7.2.

Embodiment 9

The lysis solution according to any one of embodiments 1-8, wherein said NaCl is at a concentration ranging from about 300 mM to about 500 mM, or from about 350 mM up to about 450 mM, or is about 400 mM.

Embodiment 10

The lysis solution according to any one of embodiments 1-9, wherein said chelating agent comprises an agent selected from the group consisting of N-acetyl-L-cysteine, ethylenediaminetetraacetic acid (EDTA), diethylene triamine pentaacetic acid (DTPA), ethylenediamine-N,N'-disuccinic acid (EDDS), 1,2-bis(o-aminophenoxy)ethane-N,N,N',N'-tetraacetic acid (BAPTA), and a phosphonate chelating agent.

Embodiment 11

The lysis solution according to any one of embodiments 1-10, wherein said chelating agent comprises EDTA.

Embodiment 12

The lysis solution according to any one of embodiments 1-11, wherein the concentration of said chelating agent in said solution ranges from about 5 mM to about 100 mM, or from about 10 mM to about 50 mM, or is about 25 mM.

Embodiment 13

The lysis solution according to any one of embodiments 1-12, wherein the concentration of said MgCl$_2$ ranges from about 2 mM up to about 20 mM, or from about 5 mM up to about 15 mM, or is about 10 mM.

Embodiment 14

The lysis solution according to any one of embodiments 1-13, wherein said detergent is an ionic detergent or a non-ionic detergent.

Embodiment 15

The lysis solution according to any one of embodiments 1-13, wherein said detergent comprises a detergent selected from the group consisting of N-lauroylsarcosine, sodium dodecyl sulfate (SDS), cetyl methyl ammonium bromide (CTAB), TRITON®-X-100, n-octyl-β-D-glucopyranoside, CHAPS, n-octanoylsucrose, n-octyl-β-D-maltopyranoside, n-octyl-β-D-thioglucopyranoside, PLURONIC® F-127, TWEEN® 20, and n-heptyl-β-D-glucopyranoside.

Embodiment 16

The lysis solution of embodiment 13, wherein said detergent comprises TWEEN® 20.

Embodiment 17

The lysis solution according to any one of embodiments 1-16, wherein said detergent comprises about 0.1% to about 2% of said solution, or about 0.5% to about 1.5% of said solution, or about 1% of said solution.

Embodiment 18

The lysis solution according to any one of embodiments 4-17, wherein said antifoaming agent comprises an organic antifoam emulsion or a siloxane based antifoam emulsion.

Embodiment 19

The lysis solution of embodiment 18, wherein said antifoaming agent comprises a siloxane emulsion.

Embodiment 20

The lysis solution of embodiment 18, wherein said antifoaming agent comprises a 10% emulsion of an active silicon antifoam and non-ionic emulsifiers (SE-15).

Embodiment 21

The lysis solution according to any one of embodiments 4-20, wherein said antifoaming agent is present at an amount ranging from about 0.001% up to about 0.05%, or ranging from about 0.005% up to about 0.03%, or from about 0.008% up to about 0.02% of said lysis solution, or is present at an amount of about 0.01% of said lysis solution.

Embodiment 22

The lysis solution according to any one of embodiments 5-17, wherein said biocide comprise one or more agents selected from the group consisting of sodium azide, sodium dehydroacetate, sodium borate decahydrate, and disodium edetate.

Embodiment 23

The lysis solution of embodiment 22, wherein said biocide comprises sodium azide.

Embodiment 24

The lysis solution according to any one of embodiments 5-23, wherein said biocide is present at an amount ranging from about 0.001% up to about 0.05%, or ranging from about 0.005% up to about 0.03%, or from about 0.008% up to about 0.02% of said lysis solution, or is present at an amount of about 0.01% of said lysis solution.

Embodiment 25

The lysis solution of embodiment 1, wherein said solution comprises: about 400 mM NaCl; about 50 mM HEPES sodium salt (MW 260.29); about 25 mM EDTA; about 10 mM $MgCl_2$; and about 1% Tween 20.

Embodiment 26

The lysis solution of embodiment 25, wherein the pH of said solution ranges from about 6.90 to about 7.25.

Embodiment 27

The lysis solution of embodiment 25, wherein the pH of said solution ranges from about 6.95 to about 7.15.

Embodiment 28

The lysis solution according to any one of embodiments 25-27, wherein said solution comprises about 0.01% anti-foaming agent.

Embodiment 29

The lysis solution of embodiment 28, wherein said anti-foaming agent is SE-15.

Embodiment 30

The lysis solution according to any one of embodiments 25-29, wherein said solution comprises about 0.01% sodium azide.

Embodiment 31

The lysis solution according to any one of embodiments 1-30, wherein said solution further comprises a protease.

Embodiment 32

The lysis solution of embodiment 31, wherein said protease is selected from the group consisting of proteinase K, trypsin, chymotrypsin, and papain.

Embodiment 33

The lysis solution of embodiment 31, wherein said protease is Proteinase K.

Embodiment 34

The lysis solution according to any one of embodiments 31-33, wherein said protease ranges in concentration from of 14 mg/mL to about 22 mg/mL and is added to said lysis solution at amount ranging from about 10 μL up to about 100 or from about 20 μL up to about 50 μL, or about 20 μL up to about 40 μL.

Embodiment 35

A method for extracting a nucleic acid from a cell or tissue sample, said method comprising: incubating one or more cell or tissue samples in a lysis solution according to any one of embodiments 1-34, wherein said incubating is at a temperature ranging from about 50° C. to about 100° C. and said incubation is for a time ranging from about 10 minutes up to about 24 hours.

Embodiment 36

The method of embodiment 35, wherein said temperature is from about 60° C. to about 90° C., or from about 70° C. to about 90° C., or from about 75° C. to about 85° C., or about 80° C.

Embodiment 37

The method according to any one of embodiments 35-36, wherein said incubating is for a time ranging from about 15 minutes up to about 12 hours, or from about 20 minutes up to about 8 hours, or from about 30 minutes up to about 6 hours, or from about 30 minutes up to about 4 hours, or from about 30 minutes up to about 2 hours, or for about 15 min, or for about 30 min, or for about 45 min, or for about 60 min, or for about 90 min, or for about 120 min.

Embodiment 38

The method according to any one of embodiments 35-37, wherein said method further comprises recovering said nucleic acid from said lysis solution.

Embodiment 39

The method of embodiment 38, wherein said recovering comprises the addition of a lower alcohol to said solution.

Embodiment 40

The method of embodiment 39, wherein said lower alcohol comprises ethanol or isopropanol.

Embodiment 41

The method of embodiment 39, wherein said lower alcohol comprises ethanol.

Embodiment 42

The method according to any one of embodiments 35-41, wherein said nucleic acid is a deoxyribonucleic acid (DNA).

Embodiment 43

The method according to any one of embodiments 35-41, wherein said nucleic acid is a ribonucleic acid (RNA).

Embodiment 44

The method according to any one of embodiments 35-43, wherein said cell or tissue sample(s) are selected from the group consisting of tissue biopsies, an aspirates, a cell smears, a wipe, a scrape, an archived sample, a fixed tissue section, a cryosection, a cell button, and a tissue microarray.

Embodiment 45

The method of embodiment 44, wherein said cell or tissue sample(s) comprise a sample obtained from a punch biopsy.

Embodiment 46

The method of embodiment 44, wherein said cell or tissue sample(s) comprise a sample obtained from a buccal scrape, or a gynecological scrape.

Embodiment 47

The method of embodiment 44, wherein said cell or tissue sample(s) comprise a sample obtained using a device selected from the group consisting of a multispatula, an extended tip spatula, a cytobrush, a cytopick, a cervexbrush, swab, a baynebrush, a profilebrush, a bulb aspirator, an Ayre spatula, and an Aylesbury device.

Embodiment 48

The method of embodiment 44, wherein said cell or tissue sample(s) comprise a fine needle aspirate and/or a cell smear.

Embodiment 49

The method of embodiment 44, wherein said cell or tissue sample(s) comprise fixed paraffin embedded tissue samples.

Embodiment 50

The method of embodiment 44, wherein said cell or tissue sample(s) comprise formalin fixed paraffin embedded tissue samples.

Embodiment 51

The method of embodiment 44, wherein said cell or tissue sample(s) comprise tissue section(s).

Embodiment 52

The method of embodiment 51, wherein said tissue section(s) range in thickness from about 1 μm to about 15 μm.

Embodiment 53

The method of embodiment 52, wherein said tissue section(s) having a thickness of about 8 μm or less, or about 6 μm or less, or about 5 μm or less, or about 4 μm or less, or about 3 μm or less, or about 2 μm or less.

Embodiment 54

The method according to any one of embodiments 35-53, wherein said tissue sample(s) are from a cancerous tissue.

Embodiment 55

The method of embodiment 54, wherein said tissue sample comprises a sample from a cancer selected from the group consisting of ovarian cancer, pancreatic cancer, lung cancer, hepatocarcinoma, melanoma, retinoblastoma, breast cancer, colorectal cancer, testicular cancer, leukemia, lymphoma, brain tumor, cervical carcinoma, sarcoma, prostate tumor, bladder tumor, tumor of reticuloendothelial tissue, Wilm's tumor, astrocytoma, glioblastoma, neuroblastoma, ovarian carcinoma, osteosarcoma, renal cancer, and head and neck cancer.

Embodiment 56

The method according to any one of embodiments 35-55, wherein said method does not include further steps of deparaffinization and/or additional reagents for deparaffinization.

Embodiment 57

The method according to any one of embodiments 35-56, wherein said method does not utilize an organic solvent for deparaffinization.

Embodiment 58

The method according to any one of embodiments 35-57, wherein said incubating is not in the presence of an organic solvent.

Embodiment 59

The method according to any one of embodiments 35-58, wherein the lysed tissue sample is mixed with a lower alcohol and stored.

Embodiment 60

The method of embodiment 59, wherein said lower alcohol comprises ethanol or isopropanol.

Embodiment 61

The method of embodiment 59, wherein said lower alcohol comprises ethanol.

Embodiment 62

The method according to any one of embodiments 59-61, wherein said tissue sample(s) are stored at a temperature of −20° C. or lower.

Embodiment 63

The method according to any one of embodiments 59-62, wherein the lysis solution is stored over a period of at least 6 hours, or over a period of at least one day, or over a period of at least two days, or over a period of at least 4 days, or over a period of at least one week, or over a period of at least two weeks, or over a period of at least one month, or over a period of at least two months, or over a period of at least three months, or over a period of at least 6 months, or over a period of at least one year, or over a period of at least two years, or over a period of at least 5 years and in later RT-PCR provides consistent cycle thresholds.

Embodiment 64

The method according to any one of embodiments 35-63, wherein said method further comprises amplifying all or a portion of said nucleic acid.

Embodiment 65

The method of embodiment 64, wherein said method further comprising utilizing said nucleic acid as a template in a PCR amplification.

Embodiment 66

The method of embodiment 64, wherein said method further comprising utilizing said nucleic acid in RT PCR.

Embodiment 67

The method of embodiment 64, wherein said method further comprising amplifying said nucleic acid in a GeneXpert system.

Embodiment 68

The method according to any one of embodiments 35-67, wherein said nucleic acid is used to determine the presence and/or expression level of expression of at least one target RNA that is an mRNA.

Embodiment 69

The method according to any one of embodiments 35-67, wherein said nucleic acid is used to determine the presence and/or expression level of expression of at least one target RNA selected from the group consisting of KRT20, IGF2, ANXA10, CRH, ABL, ERBB1, ERBB2, ERBB3, ERBB4, ESR1, PGR, MPO, CDKN2A, MKI67, TOP2A, MCM5, BIRC5, MMP9, and MCM2, PTEN, APC, KRAS, GATA3, PIC3CA, MAP3K1, TP53, and mutations of any of these.

Embodiment 70

The method according to any one of embodiments 35-69, where nucleic acids are amplified from the original lysed samples two or more different times.

Embodiment 71

The method of embodiment 70, wherein said two or more different times are over a period at least 6 hours, or over a period of at least one day, or over a period of at least two days, or over a period of at least 4 days, or over a period of at least one week, or over a period of at least two weeks, or over a period of at least one month, or over a period of at least two months, or over a period of at least three months, or over a period of at least 6 months, or over a period of at least one year, or over a period of at least two years, or over a period of at least 5 years.

Embodiment 72

The method according to any one of embodiments 70-71, wherein a second or later amplification comprise a repeat test.

Embodiment 73

The method according to any one of embodiments 70-71, wherein a second or later amplification comprise a reflex cartridge test.

Embodiment 74

A method for quantitative measurement of gene expression of a target gene in a fixed paraffin embedded tissue sample comprising: extracting an RNA from a formalin-fixed paraffin-embedded biological tissue sample according to the method of any one of embodiments 35-73; subjecting the extracted nucleic acid to amplification using a pair of oligonucleotide primers capable of amplifying a region of a target gene mRNA, to obtain an amplified sample; and determining the presence and/or quantity of said target gene mRNA.

Embodiment 75

The method of embodiment 74, wherein the quantity of said target gene mRNA is determined relative to the quantity of an internal control gene's mRNA from the isolated mRNA.

Embodiment 76

The method according to any one of embodiments 74-75, wherein determining the relative gene expression level comprises using RT-PCR.

Embodiment 77

The method according to any one of embodiments 74-76, wherein the internal control gene is β-actin.

Embodiment 78

The method according to any one of embodiments 74-77, wherein said target gene is selected from the group consisting of an ALK gene rearrangement, alpha-fetoprotein (AFP), Beta-2-microglobulin (B2M), beta-human chorionic gonadotropin (beta-hCG), BCR-ABL fusion gene, BRAF mutation V600E, CA15-3/CA27.29, CA19-9, CA-125, calcitonin, carcinoembryonic antigen (CEA), CD20, chromogranin A (CgA), chromosome 3, chromosome 7, chromosome 17, chromosome 9p21, chromosome 20q13, cytokeratin fragments 21-1, EGFR mutation analysis, estrogen receptor (ER), progesterone receptor (PR), fibrin/fibrinogen, HE4, HER4, HER2/neu, KIT, KRAS mutation analysis, lactate dehydrogenase, nuclear matrix protein 22, prostate-specific antigen (PSA), thyroglobulin, urokinase plasminogen activator (uPA), and plasminogen activator inhibitor (PAI-1).

Embodiment 79

A kit for the extraction of a nucleic acid from a cell and/or tissue sample, said kit comprising a container containing a lysis solution according to any one of embodiments 1-30.

Embodiment 80

The kit of embodiment 79, wherein said kit further comprises a container containing a protease.

Embodiment 81

The kit of embodiment 80, wherein said protease is selected from the group consisting of proteinase K, trypsin, chymotrypsin, and papain.

Embodiment 82

The kit of embodiment 80, wherein said protease is proteinase K.

Embodiment 83

The kit according to any one of embodiments 80-82, wherein said protease and said lysis solution mixed together.

Embodiment 84

The kit according to any one of embodiments 80-82, wherein said protease and said lysis solution are provided in separate containers.

Embodiment 85

The kit according to any one of embodiments 79-84, wherein said kit further comprises a device for the collection of a cell or tissue sample.

Embodiment 86

The kit of embodiment 85, wherein said kit comprises a device selected from the group consisting of a device or device tip for performing a scrape, a wipe, a device or device tip for obtaining an aspirate, a punch biopsy device, and a blade for obtaining a skin biopsy.

Embodiment 87

The kit of embodiment 86, wherein said kit comprises a device or device tip for obtaining a fine needle aspirate.

Embodiment 88

The kit of embodiment 86, wherein said kit comprises a device or device tip for obtaining a vacuum assisted aspirate.

Embodiment 89

The kit of embodiment 86, wherein said kit comprises a device for performing a buccal scrape, or a gynecological scrape.

Embodiment 90

The kit of embodiment 86, wherein said kit comprises a device selected from the group consisting of a multispatula, an extended tip spatula, a cytobrush, a cytopick, a cervexbrush, swab, a baynebrush, a profilebrush, a bulb aspirator, an Ayre spatula, and an Aylesbury device.

Embodiment 91

The kit according to any one of embodiments 79-90, wherein said kit comprises a container configured to receive a cell or tissue sample and to store that sample in said lysis solution or in a buffer.

Embodiment 92

The kit of embodiment 91, wherein said container configured to receive a cell or tissue sample is configured for storage and/or shipping.

BRIEF DESCRIPTION OF THE DRAWINGS

FIG. 2A shows cycle threshold as a function of NaCl concentration for ESR and PGR. FIG. 2B shows cycle threshold as a function of NaCl concentration for ERBB2 and CYFIP1. FIG. 2C shows cycle threshold as a function of NaCl concentration for MKi67.

FIG. 3A shows the stability (repeatable of cycle threshold) for ESR, and PGR for samples stored over 62 days. FIG. 3B shows the stability (repeatable of cycle threshold) for ESR, and PGR for samples stored over 62 days.

DETAILED DESCRIPTION

Figure 1:
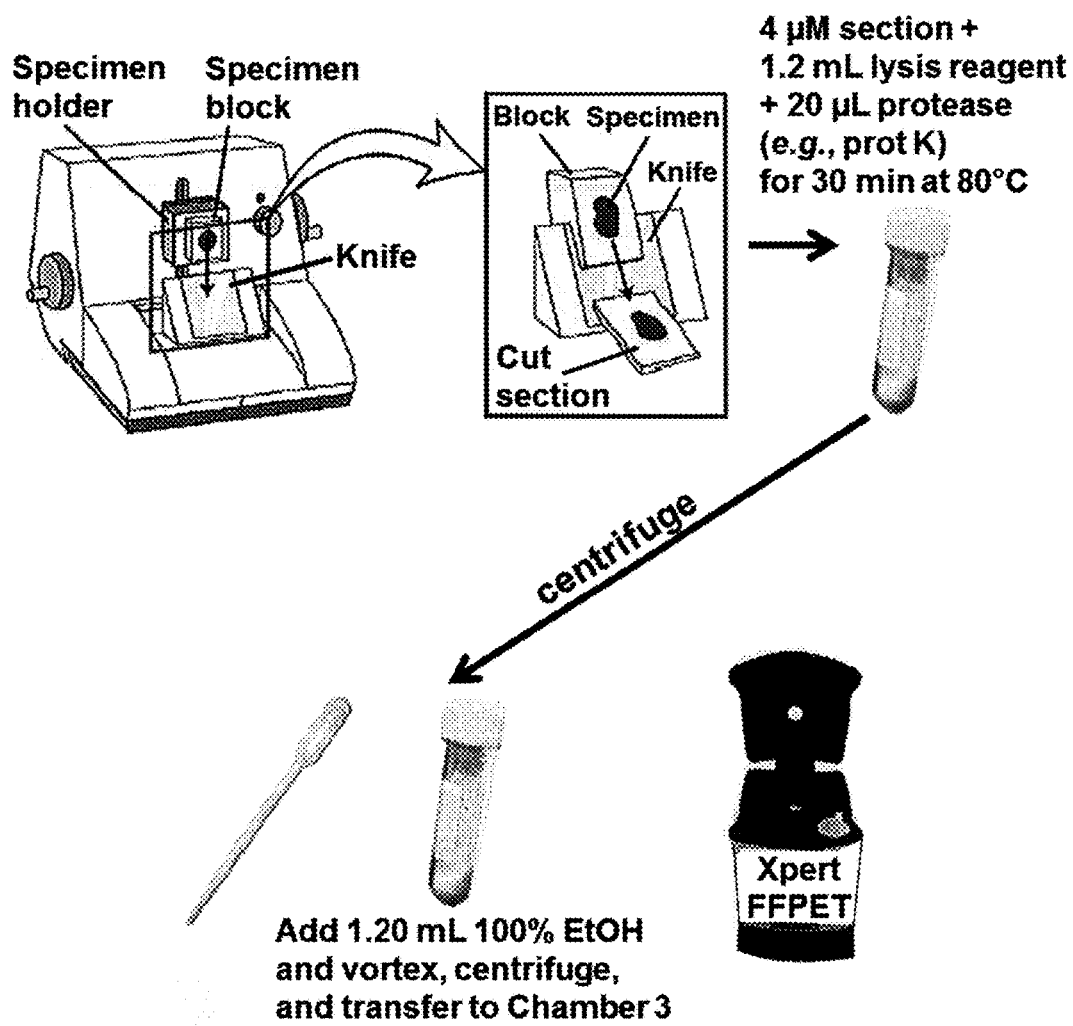
FIG. 1 schematically illustrates one embodiment of an FFPET GENEXPERT® workflow.

Formalin-fixed, paraffin-embedded tissue (FFPET) samples represent the most commonly collected and stored samples for use in the diagnosis and prognosis of diseases, including, but not limited to, cancer. Nevertheless, historically these samples have been underutilized for the purpose of gene expression profiling because of the poor quality and quantity of FFPET nucleic acids. The analysis of nucleic acids from formalin fixed, paraffin embedded tissue (FFPET) is challenging due to the multiple steps required for generating amplifiable (e.g., PCR-amplifiable) genetic material. The procedure to isolate nucleic acids from FFPET has typically involved removal of paraffin (deparaffinization), lysis of preserved sample (protease digestion), reversal of cross-links acquired during the fixation process, and solid phase-based purification of nucleic acids.

There are various sample-prep procedures for extracting PCR-ready DNA/RNA, but most are complex and labor intensive. The compositions and methods described herein overcome these and other problems and provide reagents and protocols that can be used to rapidly isolate amplifiable quality nucleic acid samples (e.g., DNA, RNA). The methods provided are simple, easily semi- or fully-automated, and require requiring minimal hands-on time. The nucleic acids are extracted at high yield and are of PCR-amplifiable quality.

In certain embodiments, a lysis solution is provided that can be used to extract nucleic acids from a paraffin embedded formalin fixed sample using a single solution and incubation at a single temperature. This is provides a significant improvement is simplicity, efficiency and cost over previous two buffer/two temperature systems used to isolate nucleic acids from tissue samples.

It will be noted that while the discussion below focuses on FFPE samples, the lysis reagents described herein and uses thereof are effective with essentially any cellular or tissue sample including, but not limited to, fresh tissue sections, frozen tissue sections, cell biopsies, needle aspirates, cell buttons, tissue microarrays, and the like.

Lysis Solution.

In certain embodiments the lysis solutions comprise a high concentration sodium salt (e.g., NaCl), a buffer sufficient to maintain the pH of the solution at a pH ranging from about pH 6.5 to about pH 7.5, or from about pH 6.8 to about pH 7.3, a chelating agent, a magnesium salt (e.g., $MgCl_2$), and a detergent. In certain embodiments the lysis solution additionally contains an antifoaming agent, and/or a preservative/biocide, and/or a protease. In certain embodiments the lysis solution omits the protease which can then be added immediately prior to use.

One illustrative, but non-limiting embodiment of a lysis solution is shown in Table 1.

TABLE 1

Illustrating, but non-limiting lysis solution.

| Component | Concentration | Description |
|---|---|---|
| NaCl (MW 58.44) | 400 mM | Sodium salt |
| Tween 20 | 1% | Detergent |
| $MgCl_2$ (MW 95.21) | 10 mM | Magnesium salt |
| EDTA (MW 372.24) | 25 mM | Chelating agent |
| HEPES sodium salt (MW 260.29) | 50 mM | Buffer |
| Sodium azide (w/v) | 0.01% | Preservative/biocide |
| Antifoam SE-15* | 0.01% | Antifoaming Agent |
| pH | 7.05 (+/−0.1) | |

This formulation is intended to be illustrative, but non-limiting. Using the teachings provided herein, other lysis solutions useful for a 1-step, 1 temperature extraction of nucleic acids from a tissue sample will be available to one of skill in the art.

Sodium Salt.

In various embodiments the lysis solution comprises a sodium salt (NaCl). In certain embodiments the sodium salt is at a concentration ranging from about 300 mM to about 500 mM, or from about 350 mM up to about 450 mM, or is about 400 mM. In certain embodiments a calcium salt (e.g., CaCl) may be used in addition to or instead of a sodium salt.

Buffer

In some embodiments, the lysis solution comprises a buffer that buffers the solution at a pH ranging from about pH 6.5 up to about pH 7.5. In some embodiments the buffer buffers the solution at a pH ranging from about pH 6.6, or about pH 6.7, or about pH 6.8 up to about pH 7.5 or up to about pH 7.4, or up to about pH 7.3, or up to about pH 7.2. In certain embodiments the pH is buffered at pH 7.05 (+/−0.1).

In certain embodiments, the concentration of the buffer ranges from about 10 mM up to about 100 mM, or from about 20 mM up to about 50 mM, or is about 50 mM In certain embodiments any of a number of buffers used in biology are suitable. Such include, but are not limited to buffers such as citrate buffer, Tris, phosphate, PBS, citrate, TAPS, Bicine, Tricine, TAPSO, HEPES, TES, MOPS, PIPES, Cacodylate, SSC, MES, and the like. An illustrative, but non-limiting list of buffer compounds is provided in Table 2.

TABLE 2

Common buffers that can be used in a lysis solution.

| Common Name | $pK_a$ at 25° C. | Buffer Range | Full Compound Name |
|---|---|---|---|
| TAPS | 8.43 | 7.7-9.1 | 3-{[tris(hydroxymethyl)methyl]amino}propanesulfonic acid |
| Bicine | 8.35 | 7.6-9.0 | N,N-bis(2-hydroxyethyl)glycine |
| Tris | 8.06 | 7.5-9.0 | tris(hydroxymethyl)methylamine |
| Tricine | 8.05 | 7.4-8.8 | N-tris(hydroxymethyl) methylglycine |
| TAPSO | 7.635 | 7.0-8.2 | 3-[N-Tris(hydroxymethyl)methyl-amino]-2-hydroxypropanesulfonic Acid |
| HEPES | 7.48 | 6.8-8.2 | 4-2-hydroxyethyl-1-piperazineethane-sulfonic acid |
| TES | 7.40 | 6.8-8.2 | 2-{[tris(hydroxymethyl)methyl]amino}-ethanesulfonic acid |
| MOPS | 7.20 | 6.5-7.9 | 3-(N-morpholino)propanesulfonic acid |
| PIPES | 6.76 | 6.1-7.5 | piperazine-N,N'-bis(2-ethanesulfonic acid) |
| Cacodylate | 6.27 | 5.0-7.4 | dimethylarsinic acid |
| SSC | 7.0 | 6.5-7.5 | saline sodium citrate |
| MES | 6.15 | 5.5-6.7 | 2-(N-morpholino)ethanesulfonic acid |
| Citrate | | | Sodium citrate |

In one illustrative, but non-limiting embodiment, the buffer is a HEPES HEPES sodium salt (MW 260.29) present at about 50 mM.

The various buffers described above are intended to be illustrative and not limiting. Using the teaching and examples provided herein, numerous other buffers for use in a lysis solution in accordance with the methods described herein will be available to one of skill in the art.

Chelating Agent.

As indicated above, in some embodiments, the lysis solution comprises one or more chelating agents. Chelating agents are well known to those of skill in the art and include, but are not limited to N-acetyl-L-cysteine, ethylenediaminetetraacetic acid (EDTA), diethylene triamine pentaacetic acid (DTPA), ethylenediamine-N,N'-disuccinic acid (EDDS), 1,2-bis(o-aminophenoxy)ethane-N,N,N',N'-tetraacetic acid (BAPTA), and phosphonate chelating agents (e.g., including, but not limited to nitrilotris(methylene) phosphonic acid (NTMP), ethylenediamine tetra(methylene phosphonic acid) (EDTMP), diethylenetriamine penta(methylene phosphonic acid (DTPMP), 1-hydroxy ethylidene-1,1-diphosphonic acid (HEDP), and the like). In some embodiments the chelating agent comprises EDTA, or DTAP. In some embodiments, the chelating agent comprises EDTA.

In some embodiments, when present, the chelating agent is present in the lysis solution at a concentration ranging from about 5 mM up to about 200 mM, or from about 10 mM up to about 100 mM. In some embodiments, the chelating agent is present at a concentration ranging from about 10 mM, or from about 20 mM, or from about 30 mM, or from about 40 mM up to about 60 mM, or up to about 70 mM, or up to about 80 mM, or up to about 90 mM, or up to about 100 mM. In some embodiments, the chelating agent is present at a concentration of about 50 mM. In some embodiments, the chelating agent ranges from about 1 mM up to about 140 mM, or from about 5 mM up to about 100 mM, or from about 10 mM to about 50 mM, or is about 25 mM.

Magnesium Salt.

In certain embodiments the lysis solution contains a magnesium salt. In certain embodiments the magnesium salt is $MgCl_2$. In certain embodiments the concentration of the magnesium salt in the lysis solution ranges from about 2 mM up to about 20 mM, or from about 5 mM up to about 15 mM, or is about 10 mM.

Detergent

As indicated above, in some embodiments, the lysis solution comprises one or more detergents. In some embodiments, the detergent comprises an ionic detergent or a non-ionic detergent. In some embodiments, the detergent includes one or more detergents shown in Table 3.

TABLE 3

Illustrative, but non-limiting detergents for use in some embodiments of the lysis solution described herein.

| Description | M | Formula | Class |
| --- | --- | --- | --- |
| Benzethonium chloride | 448.08 | $C_{27}H_{42}ClNO_2$ | cationic |
| BRIJ ® 35 | 1198.56 | $C_{58}H_{118}O_{24}$ | nonionic |
| BRIJ ® 58 | 1123.51 | $C_{56}H_{114}O_{21}$ | nonionic |
| Cetylpyridinium chloride monohydrate | 358.01 | $C_{21}H_{38}ClN \cdot H2O$ | cationic |
| Cetyltrimethylammonium bromide | 364.46 | $C_{19}H_{42}BrN$ | cationic |
| CHAPS | 614.89 | $C_{32}H_{58}N2O7S$ | zwitterionic |
| CHAPSO | 630.87 | $C_{32}H_{58}N2O8S$ | zwitterionic |
| 1-Decanesulfonic acid sodium salt | 244.33 | $C_{10}H_{21}NaO3S$ | anionic |
| n-Decyl-β-D-glucopyranoside | 320.43 | $C_{16}H_{32}O_6$ | nonionic |
| n-Decyl-β-D-maltoside | 482.57 | $C_{22}H_{42}O_{11}$ | nonionic |
| Deoxy-BIGCHAP | 862.07 | $C_{42}H_{75}N_3O_{16}$ | nonionic |
| Digitonin | 1229.34 | $C_{56}H_{92}O_{29}$ | nonionic |
| 1-Dodecanesulfonic acid sodium salt | 272.38 | $C_{12}H_{35}NaO_3S$ | anionic |
| n-Dodecyl-β-D-glucopyranoside | 348.48 | $C_{18}H_{36}O_6$ | nonionic |
| Dodecyl-β-D-maltoside | 510.63 | $C_{24}H_{46}O_{11}$ | nonionic |
| Dodecyltrimethylammonium bromide | 308.35 | $C_{15}H_{34}BrN$ | cationic |
| HECAMEG | 335.39 | $C_{15}H_{29}NO_7$ | nonionic |
| 1-Heptanesulfonic acid sodium salt anhydrous | 202.25 | $C_7H_{15}NaO_3S$ | anionic |
| 1-Heptanesulfonic acid sodium salt monohydrate | 220.27 | $C_7H_{15}NaO_3S \cdot H2O$ | anionic |
| 1-Hexanesulfonic acid sodium salt anhydrous | 188.22 | $C_6H13NaO_3S$ | anionic |
| 1-Hexanesulfonic acid sodium salt monohydrate | 206.24 | $C_6H_{13}NaO_3S \cdot H2O$ | anionic |
| n-Lauroylsarcosine sodium salt | 293.39 | $C_{15}H_{28}NNaO3$ | anionic |
| Lithium dodecylsulfate (LiDS) | 272.33 | $C_{12}H_{25}LiO_4S$ | anionic |
| MEGA-8 | 321.42 | $C_{15}H_{31}NO_6$ | nonionic |
| MEGA-9 | 335.44 | $C_{16}H_{33}NO_6$ | nonionic |
| 1-Nonanesulfonic acid sodium salt | 230.30 | $C_9H_{19}NaO_3S$ | anionic |
| n-Nonyl-β-D-glucopyranoside | 306.40 | $C_{15}H_{30}O_6$ | nonionic |
| n-Nonyl-β-D-maltoside | 468.41 | $C_{21}H_{40}O_{11}$ | nonionic |
| 1-Octanesulfonic acid sodium salt | 216.28 | $C_8H_{17}NaO_3S$ | anionic |
| n-Octyl-β-D-glucopyranoside | 292.38 | C14H28O6 | nonionic |
| n-Octyl-β-D-thioglucopyranoside | 308.44 | $C_{14}H_{28}O_5S$ | nonionic |
| Octyl-D-glucopyranoside | 292.38 | $C_{14}H_{28}O6$ | nonionic |
| 1-Pentanesulfonic acid sodium salt anhydrous | 174.20 | $C_5H_{11}NaO_3S$ | anionic |
| 1-Pentanesulfonic acid sodium salt monohydrate | 192.12 | $C_5H_{11}NaO_3S \cdot H2O$ | anionic |
| PLURONIC ® F-68 | ~8350 | | nonionic |
| Saponin | | | nonionic |
| SDS (Sodium dodecylsulfate) | 288.38 | $C_{12}H_{25}NaO_4S$ | anionic |
| Sodium cholate | 430.57 | $C_{24}H_{39}NaO_5$ | anionic |
| Sodium deoxycholate | 414.57 | $C_{24}H_{39}NaO_4$ | anionic |
| Sucrose monolaurate | 524.60 | $C_{24}H_{44}O_{12}$ | nonionic |
| Sulfobetaine SB 12 | 335.55 | $C_{17}H_{37}NO_3S$ | zwitterionic |
| Sulfobetaine SB 14 | 363.60 | $C_{19}H_{41}NO_3S$ | zwitterionic |
| n-Tetradecyl-β-D-maltoside | 538.63 | $C_{26}H_{50}O_{11}$ | nonionic |
| n-Tridecyl-β-D-maltoside | 524.64 | $C_{25}H_{48}O_{11}$ | nonionic |
| TRITON ® X-100 | 646.85 | $C_{34}H_{62}O_{11}$ | nonionic |

TABLE 3-continued

Illustrative, but non-limiting detergents for use in some embodiments of the lysis solution described herein.

| Description | M | Formula | Class |
| --- | --- | --- | --- |
| TRITON ® X-114 | 558.75 | $C_{30}H_{54}O_9$ | nonionic |
| TWEEN ® 20 | 1227.72 | $C_{58}H_{114}O_{26}$ | nonionic |
| TWEEN ® 80 | 1310 | | nonionic |
| n-Undecyl-β-D-maltoside | 496.59 | $C_{23}H_{44}O_{11}$ | Nonionic |
| N-Lauroylsarcosine | | $CH_3(CH_2)_{10}CON(CH_3)CH_2COOH$ | anionic |

In some embodiments the detergent comprises Tween 20, full strength.

In some embodiments, when present, the detergent is present in the lysis solution at a concentration ranging from about 5 mM up to about 200 mM, or from about 10 mM up to about 100 mM, or from about 20 mM up to about 50 mM, or from about 30 mM up to about 40 mM. In some embodiments the detergent ranges from about 5 mM, or from about 10 mM, or from about 15 mM or from about 20 mM or from about 25 mM up to about 200 mM or up to about 150 mM, or up to about 100 mM, or up to about 75 mM, or up to about 50 mM, or up to about 40 mM. In some embodiments, the detergent is present at a concentration of about 35 mM. In some embodiments, the detergent is present at a percentage ranging from about 0.5% (v/v) up to about 30% (v/v), or from about 1% (v/v) up to about 20% (v/v) or from about 5% up to about 15% (v/v). In some embodiments the detergent comprises about 0.1% to about 2% of said solution, or about 0.5% to about 1.5% of said solution, or about 1% of the lysis solution.

In some embodiments, the detergents used in the lysis solutions described herein need not be limited to the detergents described above. Using the teaching and examples provided herein, other detergents will be available to one of skill in the art.

Additional Components

In some embodiments, the lysis solution additionally comprises one or more of the following: a second detergent, a chaotrope and/or reducing agent, calcium chloride or other salt, and/or a protease.

Protease

In some embodiments the lysis solution additionally includes one or more proteases. Suitable proteases include, but are not limited to serine proteases, threonine proteases, cysteine proteases, aspartate proteases, metalloproteases, glutamic acid proteases, metalloproteases, and combinations thereof. Illustrative suitable proteases include, but are not limited to proteinase k (a broad-spectrum serine protease), subtilysin trypsin, chymotrypsin, pepsin, papain, and the like.

In some embodiments, when present in the lysis solution the protease is present at an amount that provides an activity that ranges from 1 U/ml up to about 200 U/ml of lysis solution. In some embodiments, the amount provides an activity ranging from about 1 U/ml, or from about 5 U/ml, or from about 10 U/ml, or from about 15 U/ml, up to about 200 U/ml, or up to about 100 U/ml, or up to about 80 U/ml, or up to about 60 U/ml, or up to about 40 U/ml, or up to about 30 U/ml of lysis solution. In some embodiments, the amount of protease ranges from about 0.05 to about 5 mg/ml. In some embodiments, the amount of protease ranges from about 0.1 mg/mL, or about 0.2 mg/mL, or about 0.3 mg/mL, or about 0.4 mg/mL, or about 0.5 mg/mL, or about 0.6 mg/mL, or about 0.7 mg/mL, or about 0.8 mg/mL up to about 5 mg/mL, or up to about 4 mg/mL, or up to about 3 mg/mL, or up about 2 mg/Ml, or up to about 1 mg/mL.

In some embodiments, the lysis solutions in the methods described herein need not be limited to the use of the proteases described above. Using the teaching and examples provided herein, other proteases will be available to one of skill in the art.

Methods of Use.

In various embodiments methods of use of the lysis solutions described herein are provided. One embodiment of the methods is schematically illustrated in FIG. 1. As shown therein, one or more sections of a fixed, paraffin-embedded, tissue sample, are incubated in a lysis solution at a temperature ranging from about 50° C. to about 110° C., typically a single temperature of about 80° C. In certain embodiments the lysis solution lacks a protease, however, more typically a protease (e.g., proteinase K) is included.

The nucleic acids can be recovered from the lysis solution, e.g., using an alcohol extraction (e.g., an alcohol precipitation). The procedure results in a relatively high yield extraction and produces a nucleic acid (e.g., DNA, RNA) of sufficient quality for PCR amplification, detection, and/or quantification of a target nucleic acid sequence. In some embodiments the incubating is for a period of time up to about 3 hours. However, in typical embodiments, the incubating can range from about 15, 20, or 30 minutes up to about 1 hour. As noted above, in some embodiments no protease is required. Similarly, in some embodiments, the method does not include further steps of deparaffinization and/or additional reagents for deparaffinization. In some embodiments the method does not utilize an organic solvent for deparaffinization and/or the incubating is not in the presence of an organic solvent. According, the method is rapid, simple, and easily amenable to automation and high throughput methodologies.

The nucleic acids extracted using the methods and reagents described herein are of good quality and can readily be amplified to detect and/or quantify one or more target nucleic acid sequences in the sample. The nucleic acids are compatible with any of a number of amplification methods including, but not limited to polymerase chain reaction (PCR) (see. e.g., Innis, et al. (1990) *PCR Protocols. A guide to Methods and Application. Academic Press, Inc. San Diego*,) including RT-PCR, ligase chain reaction (LCR) (see, e.g., Wu and Wallace (1989) *Genomics* 4: 560; Landegren et al. (1988) *Science* 241: 1077; Barringer et al. (1990) *Gene* 89: 117), transcription amplification (see, e.g., Kwoh et al. (1989) *Proc. Natl. Acad. Sci. USA* 86: 1173), self-sustained sequence replication (see, e.g., Guatelli et al. (1990) *Proc. Nat. Acad. Sci. USA* 87: 1874), dot PCR, linker adapter PCR, and the like.

Moreover it was a surprising discovery that samples processed in accordance with the methods using the materials described herein, particularly using the lysis solution(s)

described herein (see, e.g., Table 1) give earlier Ct results, sometimes better than 2 Cts, or better than 3 Cts, or better than 4 Cts, as compared to various commercial lysis systems.

Figure 3A:
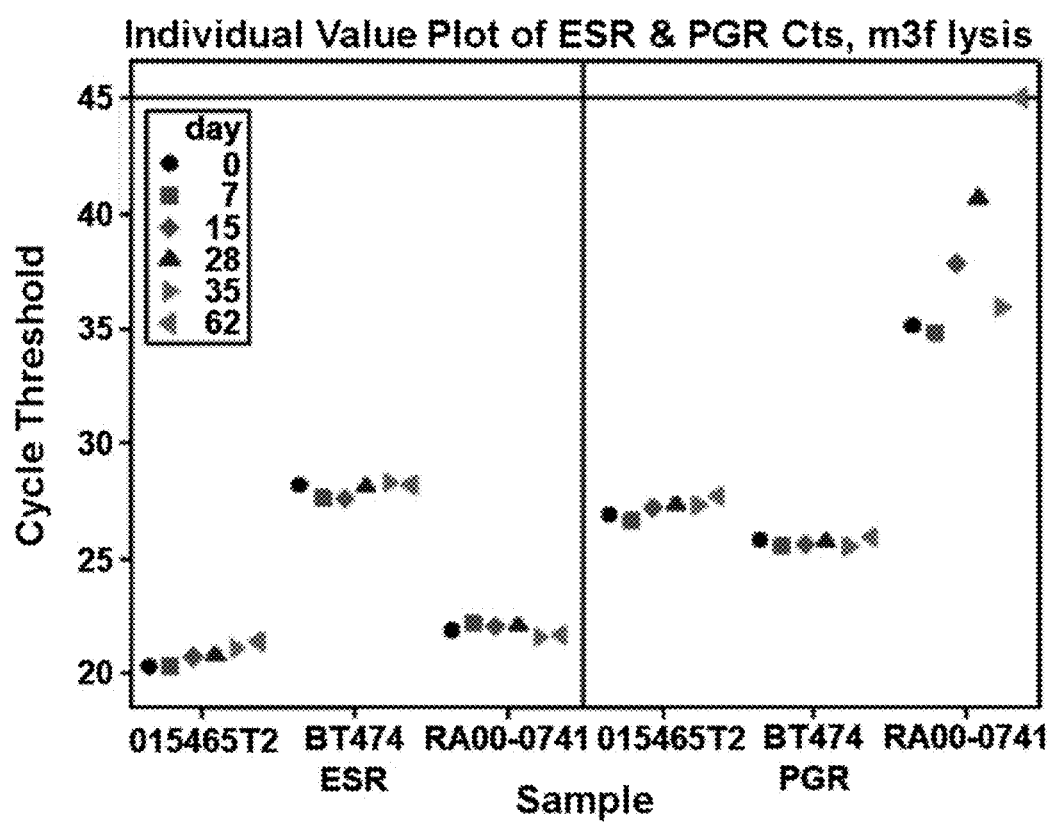
FIGS. 3A and 3B show stability of samples over time.
Figure 3B:
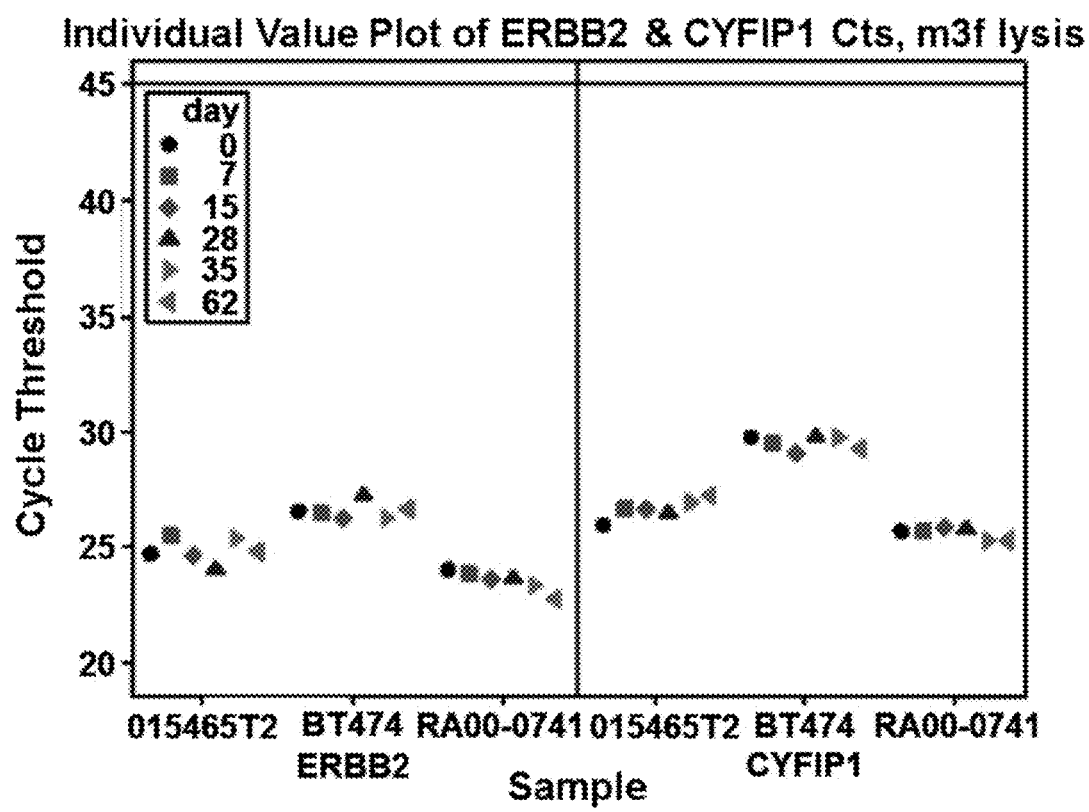

Additionally a lysate stability study was performed in which FFPE cell buttons and FPE patient samples were lysed, mixed with Ethanol and then stored at −20 C with scheduled test dates (see, e.g., Example 1, experiment G, on-going thru Day 62, and FIGS. 3A and 3B). In one experiment, presently out to 62 days consistent cycle thresholds were observed over the course of the 62 days for all targets. It is thus possible to measure multiple pulls from the original lysed scroll to perform either a repeat test (if needed) or reflex cartridge test(s).

While in some embodiments, the extracted nucleic acids are used in amplification reactions, other uses are also contemplated. Thus, for example, the extracted nucleic acids (or their amplification product(s)) can be used in various hybridization protocols including, but not limited to nucleic acid based microarrays. In some embodiments any nucleic acid-based microarray can be used with the methods described herein. Such microarrays include but are not limited to, commercially available microarrays, for example microarrays available from Affymetrix, Inc. (Santa Clara, Calif.), Agilent Technologies, Inc. (Santa Clara, Calif.), Illumina, Inc. (San Diego, Calif.), GE Healthcare (Piscataway, N.J.), NimbleGen Systems, Inc. (Madison, Wis.), Invitrogen Corp. (Carlsbad, Calif.), and the like.

The methods and reagents described herein are thus applicable to basic research aimed at the discovery of gene expression profiles relevant to the diagnosis and prognosis of disease. The methods are also applicable to the diagnosis and/or prognosis of disease, the determination particular treatment regiments, monitoring of treatment effectiveness and the like. In some embodiments the methods are also applicable to other fields where the quality of nucleic acid is poor, such as forensics, archeology, medical history, paleontology, and the like. In view of the teachings and protocols provided herein, these and other applications will readily be recognized by those of skill in the art.

Samples.

Using the methods described herein DNA and/or RNA can be isolated from any biological sample. Such samples include, but are not limited to fresh samples or cell/tissue aspirates, frozen sections, needle biopsies, cell cultures, fixed tissue samples, cell buttons, tissue microarrays, and the like. The methods are particularly well suited for use with fixed paraffin-embedded tissue (e.g., FFPET) samples. While histological samples are typically fixed with an aldehyde fixative such as formalin (formaldehyde) and glutaraldehyde, it is believed the methods described herein additionally work with tissues fixed using other fixation techniques such as alcohol immersion, and the like.

Illustrative samples include, but are not limited to, FFPET samples from human tissues, laboratory animal tissues, companion animal tissues, or livestock animal tissues. Thus, for example, the samples include tissue samples from humans including, but not limited to samples from healthy humans (e.g., healthy human tissue samples), samples from a diseased subject and/or diseased tissue, samples used for diagnostic and/or prognostic assays and the like. Suitable samples also include samples from non-human animals. FFPET samples from, for example, a non-human primate, such as a chimpanzee, gorilla, orangutan, gibbon, monkey, macaque, baboon, mangabey, colobus, langur, marmoset, lemur, a mouse, rat, rabbit, guinea pig, hamster, cat dog, ferret, fish, cow, pig, sheep, goat, horse, donkey, chicken, goose, duck, turkey, amphibian, or reptile can be used in the methods described herein.

In addition, FFPET samples of any age can be used with the methods described herein including, but not limited to, FFPET samples that are fresh, less than one week old, less than two weeks old, less than one month old, less than two months old, less than three months old, less than six months old, less than 9 months old, less than one year old, at least one year old, at least two years old, at least three years old, at least four years old, at least five years old, at least six years old, at least seven years old, at least eight years old, at least nine years old, at least ten years old, at least fifteen years old, at least twenty years old, or older.

In some embodiments the methods described herein are performed on one or more sections taken from a fixed, embedded tissue sample (e.g., an FFPET sample). The sections can be of any desired thickness. Thus, in some embodiments, both thin sections or thick sections are contemplated, including, but not limited to, sections that are less than 1 micron thick, about 1 micron thick, about 2 microns thick, about 3 microns thick, about 4 microns thick, about 5 microns thick, about 6 microns thick, about 7 microns thick, about 8 microns thick, about 9 microns thick, about 10 microns thick, about 15 microns thick, or about 20 microns thick, depending upon the desired application. In certain applications, the sections can be, for example, up to about 1 micron thick, up to about 2 microns thick, up to about 3 microns thick, up to about 4 microns thick, up to about 5 microns thick, up to about 6 microns thick, up to about 7 microns thick, up to about 8 microns thick, up to about 9 microns thick, up to about 10 microns thick, up to about 15 microns thick, up to about 20 microns thick, or up to about 25 or 30 microns thick. In some embodiments, the sections can be defined by a range of sizes, including, but not limited to, between about 1 and about 5 microns thick, between about 1 and about 20 microns thick, between about 1 and about 10 microns thick, or between about 5 and about 10 microns thick.

In many cases, the fixed embedded tissue samples (e.g., FFPET samples) comprise an area of diseased tissue, for example a tumor or other cancerous tissue. While such FFPET samples find utility in the methods described herein, FFPET samples that do not comprise an area of diseased tissue, for example FFPET samples from normal, untreated, placebo-treated, or healthy tissues, also can be used in the methods described herein. In some embodiments of the methods described herein, a desired diseased area or tissue, or an area containing a particular region, feature or structure within a particular tissue, is identified in a FFPET sample, or a section or sections thereof, prior to isolation of nucleic acids as described herein, in order to increase the percentage of nucleic acids obtained from the desired region. Such regions or areas can be identified using any method known to those of skill in the art, including, but not limited to, visual identification, staining, for example hematoxylin and eosin staining, immunohistochemical labeling, and the like. In any event, in some embodiments, the desired area of the tissue sample, or sections thereof, can be dissected, either by macrodissection or microdissection, to obtain the starting material for the isolation of a nucleic acid sample using the methods described herein.

While, in certain embodiments, the lysis reagents and methods described herein are particularly well suited for use with formalin-fixed paraffin embedded (FFPE) samples, it will be appreciated that the reagents and methods need to be limited to use with such samples. For example, in certain embodiments the lysis reagent(s) and methods described herein can be used on whole cells that are, for example, applied onto a glass slide as a smear. In certain embodiments the smears are derived from a fine needle aspirate. Smears can be a vehicle that has been associated with FNAs where the drawn sample is applied to a slide as a smear. The cells can be stained for visual observations but they can also be left unstained and simply allowed to air dry. In certain embodiments using these unstained smears cells can be scrapped off the slide and utilized with the lysis reagent and methods described herein.

In another illustrative, but non-limiting approach the fine needle aspirate cells can be injected directly into the lysis reagent. The sample can continue with the lysing procedure. In certain embodiments it is possible to transport the sample (in the lysis reagent) to a different site where the analysis procedure can be completed. In certain embodiments the fine needle aspirate sample can also be made into an FFPE cell button.

The use of fine needle aspirates provides a method of avoiding the tedious process of preparing formalin fixed paraffin embedded samples and can significantly speed up the testing process. This method may be quite useful in developing areas of the world.

In addition, to fine needle aspirates, it will also be appreciated that the reagent(s) (e.g., lysis solution) and methods of use thereof are amendable to use with essentially any method of cell collection. Such methods include, but are not limited to scrapes (e.g., buccal scrapes, gynecological scrapes, throat scrapes, scrapes during surgical procedures, etc.), wipes (obtained, for example, using a cotton swab), and aspirates including, but not limited to vacuum assisted biopsies.

In certain illustrative, but non-limiting embodiments, the sample comprises a diseased area or tissue comprising cells from a cancer. In some embodiments the cancer comprises a cancer selected from the group consisting of acute lymphoblastic leukemia (ALL), acute myeloid leukemia (AML), Adrenocortical carcinoma, AIDS-related cancers (e.g., kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, Wilm's tumor, and the like.

It will be recognized that the methods described herein are believed to be compatible with essentially any fixed (e.g., formalin fixed, glutaraldehyde fixed, etc.) paraffin embedded tissue sample. Such samples include, but are not limited to biopsies and fine needle aspirates and archived samples (e.g. tissue microarrays), and the like.

Heating

In some embodiments, one or more tissue sections are heated in the lysis solution. In this regard, it is noted that where thinner sections are used it is possible and can be desirable to utilize a plurality of sections (e.g., at least 2 sections, or at least 3 sections, or at least 4 sections, or at least 5 sections, or at least 6 sections, or at least 7 sections, or at least 8 sections, or at least 9 sections, or at least 10 sections). Particularly where the section is 5 μm thick or smaller multiple sections can be desirable.

In some embodiments, the sections are heated in the lysis solution at a temperature of about 40° C. up to about 110° C. In some embodiments the sections are heated at a temperature ranging from about 40° C., or from about 45° C., or from about 50° C., or from about 55° C., or from about 60° C., or from about 65° C., or from about 70° C., or from about 74° C. up to about 110° C., or up to about 100° C., or up to about 95° C., or up to about 90° C. In some embodiments, the sections are heated at a temperature ranging from about 80° C. to about 90° C. In certain embodiments the heating is at 80° C.

In some embodiments, the incubation time ranges from about 10 minutes up to about 4 hours. In some embodiments, the incubation time ranges from about 10 minutes, or from about 15 minutes, or from about 20 minutes, or from about 25 minutes, or from about 30 minutes up to about 24 hours, or up to about 12 hours, or up to about 6 hours, or up to about 4 hours, or up to about 3.5 hours, or up to about 3 hours, or up to about 2.5 hours, or up to about 2 hours, or up to about 1.5 hours, or up to about 1 hour. In some embodiments, the incubation time ranges from about 30 minutes up to about 1 hour.

In one illustrative, but non-limiting, embodiment the one or more sections are incubated (heated) in the lysis solution (e.g., a solution as shown in Table 1) for about 60 minutes at a temperature of about 80° C. In another illustrative, but non-limiting, embodiment the one or more sections are incubated (heated) in the lysis solution (e.g., a solution as shown in Table 1) for about 30 minutes at a temperature of about 90° C.

These heating temperatures and periods are illustrative and not intended to be limiting. Using the teaching provided herein, one of skill may optimized the protocol for a particular sample type at a particular time and temperature.

Nucleic Acid Recovery

After the tissue section(s) are heated in the lysis solution the extracted nucleic acid (e.g., DNA, RNA) can be recovered. Numerous methods for DNA and/or RNA recovery are known to those of skill in the art.

In some embodiments, the nucleic acid is precipitated and/or bound to a solid substrate. Precipitation and/or binding to a substrate is readily accomplished by use of an alcohol, for example a lower alcohol (e.g., a $C_1$-$C_6$ alcohol). In some embodiments the alcohol is ethanol or isopropanol. In some embodiments the alcohol is ethanol. It will be recognized that in some embodiments, dry alcohols can be used.

In some embodiments the alcohol is used to simply precipitate the nucleic acid(s). In some embodiments, the alcohol is used to precipitate the nucleic acids in the present of a compatible solid phase that results in binding of the nucleic acid to that solid phase.

For example, in some embodiments, the alcohol treatment is performed in the present of a glass or cellulose substrate resulting in the binding of the nuclei acid(s) to that substrate. Remaining contaminants can be washed away while retaining the recovered nucleic acids that are then ready for amplification or other uses.

In some embodiments the solid phase comprises glass, silica, or cellulose. The solid phase can be provided by the walls of a container, as a fiber (e.g., glass fiber), as a membrane (e.g., cellulose membrane), in the form of beads (e.g., microparticles, or nanoparticles, etc.), and the like.

In certain embodiments, the nucleic acid recovery can be performed in a GENEXPERT® cartridge, e.g., as described below.

Illustrative Uses of Extracted DNA and/or RNA

The nucleic acids extracted using the methods and reagents described herein are of good quality and can readily be amplified to detect and/or quantify one or more target nucleic acid sequences in the sample. The nucleic acids are particular well suited to PCR amplification reactions including, but not limited to RT-PCR. While in some embodiments, the extracted nucleic acids are used in amplification reactions, other uses are also contemplated. Thus, for example, the extracted nucleic acids (or their amplification product(s)) can be used in various hybridization protocols including, but not limited to nucleic acid based microarrays.

The nucleic extraction methods and reagents described herein are applicable to basic research aimed at the discovery of gene expression profiles relevant to the diagnosis and prognosis of disease. The methods are also applicable to the diagnosis and/or prognosis of disease, the determination particular treatment regiments, monitoring of treatment effectiveness and the like.

The methods described herein simply and efficiently produce extracted nucleic acids well suited for use in RT-PCR systems. While they can be used in any such system, in some embodiments, as illustrated herein in the Examples, the nucleic acids are particularly well suited for use in the GENEXPERT® cartridge and systems (Cepheid Systems Inc.).

The GENEXPERT® system is a closed, self-contained, fully-integrated and automated platform that represents a paradigm shift in the automation of molecular analysis, producing accurate results in a timely manner with minimal risk of contamination. The GENEXPERT® system combines on-board (in cartridge) sample preparation with real-time PCR (polymerase chain reaction) amplification and detection functions for fully integrated and automated nucleic acid analysis in a cartridge (GENEXPERT® cartridge). The system is designed to purify, concentrate, detect and identify targeted nucleic acid sequences thereby delivering answers directly from samples (see, e.g., U.S. Pat. Nos. 5,958,349, 6,403,037, 6,440,725, 6,783,736, and 6,818,185, each of which is herein incorporated by reference in its entirety). In various embodiments, components of the cartridge can include, but are not limited to, processing chambers containing reagents, filters, and capture technologies useful to extract, purify, and amplify target nucleic acids. A valve enables fluid transfer from chamber to chamber and contains nucleic acids lysis and filtration components. An optical window enables real-time optical detection (e.g., of PCR amplification products). A reaction tube can be provided that permits very rapid heating and/or thermal cycling.

In certain embodiments an illustrative GENEXPERT® cartridge comprises a plurality of chambers disposed around a central valve assembly and selectively in fluid communication with the central valve assembly where the central valve assembly is configured to accommodate a plunger that is capable of drawing fluid into or out of a chamber in fluid communication with the central valve. Rotation of the valve assembly determines which chamber are in fluid communication with the central valve.

Accordingly, in some embodiments, methods are provided for identification and/or quantitative measurement of a target nucleic acid sequence in a fixed paraffin embedded tissue sample (optionally utilizing a GENEXPERT® cartridge and system). In some embodiments the methods comprise extracting a nucleic acid (e.g., a DNA, an RNA) from a fixed paraffin embedded biological tissue sample according any of the extraction methods described herein, subjecting the extracted nucleic acid to amplification using a pair of oligonucleotide primers capable of amplifying a region of a target nucleic acid, to obtain an amplified sample; and determining the presence and/or quantity of the target nucleic acid. In some embodiments, the target nucleic acid is a DNA (e.g., a gene). In some embodiments, the target nucleic acid is an RNA (e.g., an mRNA, a non-coding RNA, and the like).

In some embodiments, the nucleic acids extracted using the methods described herein are well suited for use in diagnostic methods, prognostic methods, methods of monitoring treatments (e.g., cancer treatment), and the like. Accordingly, in some illustrative, but non-limiting embodiments, the nucleic acids extracted from fixed paraffin-embedded samples (e.g., from FFPET samples) can be used to identify the presence and/or the expression level of a gene, and/or the mutational status of a gene.

Such methods are particular well suited to identification of the presence, and/or expression level, and/or mutational status of one or more cancer markers. Accordingly, in some embodiments, the nucleic acids extracted using the methods described herein are utilized to detect the presence, and/or copy number, and/or expression level, and/or mutational status of one or more cancer markers. Illustrative, but non-limiting cancer markers are shown in Table 4.

TABLE 4

Illustrative, but non-limiting, cancer markers and associated uses.

| Cancer Marker | Cancer | Uses |
| --- | --- | --- |
| ALK gene rearrangements | Non-small cell lung cancer and anaplastic large cell lymphoma | To help determine treatment and prognosis |
| Alpha-fetoprotein (AFP) | Liver cancer and germ cell tumors | To help diagnose liver cancer and follow response to treatment; to assess stage, prognosis, and response to treatment of germ cell tumors |
| Beta-2-microglobulin (B2M) | Multiple myeloma, chronic lymphocytic leukemia, and some lymphomas | To determine prognosis and follow response to treatment |
| Beta-human chorionic gonadotropin (Beta-hCG) | Choriocarcinoma and testicular cancer | To assess stage, prognosis, and response to treatment |
| BCR-ABL fusion gene | Chronic myeloid leukemia | To confirm diagnosis and monitor disease status |
| BRAF mutation V600E | Cutaneous melanoma and colorectal cancer | To predict response to targeted therapies |
| CA15-3/CA27.29 | Breast cancer | To assess whether treatment is working or disease has recurred |
| CA19-9 | Pancreatic cancer, gallbladder cancer, bile duct cancer, and gastric cancer | To assess whether treatment is working |
| CA-125 | Ovarian cancer | To help in diagnosis, assessment of response to treatment, and evaluation of recurrence |
| Calcitonin | Medullary thyroid cancer | To aid in diagnosis, check whether treatment is working, and assess recurrence |
| Carcinoembryonic antigen (CEA) | Colorectal cancer and breast cancer | To check whether colorectal cancer has spread; to look for breast cancer recurrence and assess response to treatment |
| CD20 | Non-Hodgkin lymphoma | To determine whether treatment with a targeted therapy is appropriate |
| Chromogranin A (CgA) | Neuroendocrine tumors | To help in diagnosis, assessment of treatment response, and evaluation of recurrence |
| Chromosomes 3, 7, 17, and 9p21 | Bladder cancer | To help in monitoring for tumor recurrence |
| Cytokeratin fragments 21-1 | Lung cancer | To help in monitoring for recurrence |
| EGFR mutation analysis | Non-small cell lung cancer | To help determine treatment and prognosis |
| Estrogen receptor (ER)/progesterone receptor (PR) | Breast cancer | To determine whether treatment with hormonal therapy (such as tamoxifen) is appropriate |
| Fibrin/fibrinogen | Bladder cancer | To monitor progression and response to treatment |
| HE4 | Ovarian cancer | To assess disease progression and monitor for recurrence |
| HER2/neu | Breast cancer, gastric cancer, and esophageal cancer | To determine whether treatment with trastuzumab is appropriate |
| Immunoglobulins | Multiple myeloma and Waldenstrom macroglobulinemia | To help diagnose disease, assess response to treatment, and look for recurrence |
| KIT | Gastrointestinal stromal tumor and mucosal melanoma | To help in diagnosing and determining treatment |

TABLE 4-continued

Illustrative, but non-limiting, cancer markers and associated uses.

| Cancer Marker | Cancer | Uses |
|---|---|---|
| KRAS mutation analysis | Colorectal cancer and non-small cell lung cancer | To determine whether treatment with a particular type of targeted therapy is appropriate |
| Lactate dehydrogenase | Germ cell tumors | To assess stage, prognosis, and response to treatment |
| Nuclear matrix protein 22 | Bladder cancer | To monitor response to treatment |
| Prostate-specific antigen (PSA) | Prostate cancer | To help in diagnosis, assess response to treatment, and look for recurrence |
| Thyroglobulin | Thyroid cancer | To evaluate response to treatment and look for recurrence |
| Urokinase plasminogen activator (uPA) and plasminogen activator inhibitor (PAI-1) | Breast cancer | To determine aggressiveness of cancer and guide treatment |
| 5-Protein signature (Ova1) | Ovarian cancer | To pre-operatively assess pelvic mass for suspected ovarian cancer |
| 21-Gene signature (Oncotype DX) | Breast cancer | To evaluate risk of recurrence |
| 70-Gene signature (Mammaprint) | Breast cancer | To evaluate risk of recurrence |

In some embodiments, the target nucleic acid comprises a microRNA described in U.S. Patent Publication Nos: 2012/0171686 and 2009/0062135, which are incorporated herein by reference for the target nucleic acid sequences listed therein. In some embodiments the target nucleic acid comprises a nucleic acid marker for the presence and/or severity and/or prognosis of lung cancer. In some embodiments the target nuclei acid comprises a target nucleic acid marker for lung cancer (e.g., non-small cell lung cancer) described in in U.S. Patent Publication No 2010/0233704, which is incorporated herein by reference for the target nucleic acid sequences listed therein. In some embodiments the target nucleic acid comprises a nucleic acid marker for the presence and/or severity and/or prognosis of cervical cancer and/or cervical dysplasia. In some embodiments the target nuclei acid comprises a target nucleic acid marker for cervical dysplasia and/or cervical cancer described in in U.S. Patent Publication No 2010/0240049, which is incorporated herein by reference for the target nucleic acid sequences listed therein.

The foregoing target nucleic acids are illustrative and non-limiting. Using the teaching provided herein, numerous other target nucleic acid sequences will be available to one of skill in the art.

In some, a normal level (a "control") for each target nucleic acid (e.g., RNA) can be determined as an average (or median) level or range that is characteristic of normal cells or other reference material, against which the level measured in the sample can be compared. The determined average (or median) or range of target nucleic acid (e.g., RNA) in normal subjects can be used as a benchmark for detecting above-normal levels of target RNA indicative of a disease state (e.g., the presence of or predilection for a cancer). In some embodiments, normal levels of target nucleic acid can be determined using individual or pooled RNA-containing samples from one or more individuals, such as, in the case of cervical cancer, from patients undergoing hysterectomy for benign gynecologic disease.

In some embodiments, determining a normal level of expression of a target nucleic acid (e.g., RNA) comprises detecting a complex comprising a probe hybridized to a nucleic acid selected from a target RNA, a DNA amplicon of the target RNA, and a complement of the target RNA. That is, in some embodiments, a normal level of expression can be determined by detecting a DNA amplicon of the target RNA, or a complement of the target RNA rather than the target RNA itself. In some embodiments, a normal level of such a complex is determined and used as a control. The normal level of the complex, in some embodiments, correlates to the normal level of the target RNA.

In some embodiments, a control comprises RNA from cells of a single individual, cells known to be healthy from the same subject. In some embodiments, a control comprises RNA from a pool of cells from multiple individuals. In some embodiments, a control is drawn from anatomically and/or cytologically normal areas of the of the individual from whom the test sample was obtained. In some embodiments, a control comprises commercially-available human RNA, such as, for example in the case of cervical cancer, human cervix total RNA (Ambion; AM6992). In some embodiments, a normal level or normal range has already been predetermined prior to testing a sample for an elevated level.

In some embodiments, the normal level of target RNA can be determined from one or more continuous cell lines, typically cell lines previously shown to have expression levels of the at least one target RNA that approximate the level of expression in normal cells.

In some embodiments, a method comprises detecting the level of expression of at least one target RNA. In some embodiments, a method further comprises comparing the level of expression of at least one target RNA to a normal level of expression of the at least one target RNA. In some embodiments, a method further comprises comparing the level of expression of at least one target RNA to a control level of expression of the at least one target RNA. A control level of expression of the at least one target RNA is, in some embodiments, the level of expression of the at least one target RNA in a normal cell. In some such embodiments, a control level may be referred to as a normal level. In some embodiments, a greater level of expression of the at least one target RNA relative to the level of expression of the at least one target RNA in a normal cell indicates cervical dysplasia.

In some embodiments, the level of expression of the at least one target RNA is compared to a reference level of expression, e.g., from a confirmed neoplasia. In some such embodiments, a similar level of expression of the at least one target RNA relative to the reference sample indicates the presence of a neoplasia.

In some embodiments, a level of expression of at least one target RNA that is at least about two-fold greater than a normal level of expression of the respective at least one target RNA indicates the presence of a disease state (e.g., a cancer). In some embodiments, a level of expression of at least one target RNA that is at least about two-fold greater than the level of the respective at least one target RNA in a control sample comprised of normal cells indicates the presence of a cancer. In some embodiments, a level of expression of at least one target RNA that is at least about 3-fold, at least about 4-fold, at least about 5-fold, at least about 6-fold, at least about 7-fold, at least about 8-fold, at least about 9-fold, or at least about 10-fold greater than the level of expression of the respective at least one target RNA in a control sample comprised of normal cells indicates the presence of a cancer. In some embodiments, a level of expression of at least one target RNA that is at least about 3-fold, at least about 4-fold, at least about 5-fold, at least about 6-fold, at least about 7-fold, at least about 8-fold, at least about 9-fold, or at least about 10-fold greater than a normal level of expression of the at least one target RNA indicates the presence of a cancer.

In some embodiments, a control level of expression of a target RNA is determined contemporaneously, such as in the same assay or batch of assays, as the level of expression of the target RNA in a sample. In some embodiments, a control level of expression of a target RNA is not determined contemporaneously as the level of expression of the target RNA in a sample. In some such embodiments, the control level of expression has been determined previously.

In some embodiments, the level of expression of a target RNA is not compared to a control level of expression, for example, when it is known that the target RNA is expressed at very low levels, or not at all, in normal cells. In such embodiments, detection of a high level of the target RNA in a sample is indicative of a cancer.

Kits.

In certain embodiments kits are provided for the extraction of a nucleic acid from a cell and/or tissue sample. In certain embodiments the kit will typically comprises a container containing a lysis solution as described herein. In certain embodiments the kit further comprises a container containing a protease (e.g., proteinase K, trypsin, chymotrypsin, papain, etc.). In certain embodiments the protease and the lysis solution are mixed together. In certain embodiments the protease and the lysis solution are provided in separate containers.

In certain embodiments the kit can further comprise a device for the collection of a cell or tissue sample. Illustrative devices include, but are not limited to a device selected from the group consisting of a device or device tip for performing a scrape, a wipe, a device or device tip for obtaining an aspirate, a punch biopsy device, and a blade for obtaining a skin biopsy. For example, in certain embodiments, the kit comprises a device or device tip for obtaining a fine needle aspirate and/or for obtaining a vacuum assisted aspirate. In certain embodiments the kit comprises a device for performing a buccal scrape, or a gynecological scrape. Illustrative devices include, but are not limited to a multi-spatula, an extended tip spatula, a cytobrush, a cytopick, a cervexbrush, swab, a baynebrush, a profilebrush, a bulb aspirator, an Ayre spatula, an Aylesbury device, and the like. In typical embodiments the device for collection of a cell or tissue sample is provided in packaging that preserves sterility of the sample collecting device before use.

In certain embodiments the kit can comprise a container configured to receive a cell or tissue sample and to store that sample in said lysis solution or in a buffer. In certain embodiments the container configured to receive a cell or tissue sample is configured for storage and/or shipping. Thus, in certain embodiments, the container configured to receive a cell or tissue sample, is provided with a label to identify the sample, and, in certain embodiments sealable packaging to hold the container during storage and/or shipping and/or a shipping container.

In certain embodiments the kit can optionally further include a sterile swab (e.g., an alcohol swab) for cleaning the sample site, and/or a drying pad (e.g., a gauze pad) for drying the site, and/or a dressing (e.g. bandage) for dressing the site after obtaining the sample.

In certain embodiments, the components for a single collection operation are packaged together in a packet. Such packets can include, for example, a single use disposable sample device, optionally a sterile swab, optionally a drying pad, and optionally a dressing. In certain embodiments the kit includes at least 2 packets, or at least 3 packets, or at least 4 packets, or at least 5 packets, or at least 6 packets, or at least 7 packets, or at least 8 packets.

In certain embodiments the kit can further contain instructional materials teaching collection methods utilizing the kit components and, optionally, providing guidance to overcome problems that may occur during collection. The instructional materials can also include information and/or instructions regarding the use of the lysis reagent and/or instructions for the collection, and/or storage, and/or shipping of a cell or tissue sample. In certain embodiments the kits additionally contain reagents and/or instructions teaching the use of the lysis buffer for isolation and recovery of a nucleic acid.

Often and typically the instructional materials are provided in written form and can be printed on the kit components themselves (e.g. on the cover of a box, container, or on an envelope, or can be provided as an insert/instructional page or booklet. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Examination of Lysis Solution Parameters for Extraction of Nucleic Acids from Formalin Fixed Paraffin Embedded Tissue Experiment A Goals: Perform a Proteinase K treatment using a test buffer, followed by modified FFPE lysis on patient 015445T2.

Samples: FFPE patient slides (4), 015445T2. 4 μm thick and applied to glass slides.

IHC/FISH: ER: rich, PR: rich, HER2: amplified.

TABLE 5

Results.

| Pt 015445T2 (N = 4) | cycle threshold | | | | |
|---|---|---|---|---|---|
| | PGR | ESR | ref gene | ERBB2 | MKi67 |
| FFPE control | 31.1 | 27.3 | 30.8 | 30.0 | 31.8 |
| Qiagen kit control | 27.4 | 24.1 | 28.3 | 27.7 | 28.3 |
| Qiagen, + Depar, no Pro K | 32.8 | 28.9 | 32.7 | 31.5 | 34.0 |
| Qiagen, no Depar, + Pro K | 26.7 | 22.4 | 27.7 | 26.4 | 27.0 |
| CPHD Pro K (56 C.) + mFFPE (80 C.) | 25.8 | 21.8 | 26.2 | 25.5 | 26.5 |

| | delta Ct | | |
|---|---|---|---|
| | ESR | PGR | ERBB2 |
| FFPE control | 3.5 | −0.3 | 0.8 |
| Qiagen kit control | 4.2 | 0.9 | 0.6 |
| Qiagen, + Depar, no Pro K | 3.8 | −0.1 | 1.2 |
| Qiagen, no Depar, + Pro K | 5.2 | 1.0 | 1.3 |
| CPHD Pro K (56 C.) + mFFPE (80 C.) | 4.4 | 0.5 | 0.7 |

Experiment B

Goals: Test FFPE lysis reagent with 0.01% emulsion instead of Anti-foam on Pt 015445T2 slide.

Samples FFPE patient slide, 015445T2. 4 um thick and applied to glass slides.

IHC/FISH: ER: rich, PR: rich, HER2: amplified.

TABLE 6

Results.

| Pt 015445T2 (N = 4) | cycle threshold | | | | |
|---|---|---|---|---|---|
| | PGR | ESR | ref gene | ERBB2 | MKi67 |
| original FFPE + 0.01% AF (80 C., 60 m) | 31.1 | 27.3 | 30.8 | 30.0 | 31.8 |
| Qiagen kit control | 27.4 | 24.1 | 28.3 | 27.7 | 28.3 |
| m2FFPE w/ Proteinase K, (80 C., 30 m) | 26.5 | 22.4 | 26.9 | 26.2 | 26.9 |
| original FFPE + 0.01% emulsion (80 C., 60 m) | 30.4 | 26.4 | 30.2 | 29.6 | 31.4 |

| | delta Ct | | |
|---|---|---|---|
| | ESR | PGR | ERBB2 |
| original FFPE + 0.01% AF (80 C., 60 m) | 3.5 | −0.3 | 0.8 |
| Qiagen kit control | 4.2 | 0.9 | 0.6 |
| m2FFPE w/ Proteinase K, (80 C., 30 m) | 4.5 | 0.4 | 0.7 |
| original FFPE + 0.01% emulsion (80 C., 60 m) | 3.8 | −0.3 | 0.6 |

Experiment C

Goals: Optimize amount of PK added during off board lysis (before heat step).

Samples Alamak FFPE cell buttons, BT474.

TABLE 7

Results.

| BT474 (N = 4) | cycle threshold | | | | |
|---|---|---|---|---|---|
| | PGR | ESR | ref gene | ERBB2 | MKi67 |
| no PK | 28.5 | 30.4 | 31.3 | 28.7 | 33.6 |
| 20 uL PK (80 C., overnight) | 27.8 | 29.5 | 30.7 | 28.4 | 32.5 |
| 5 uL PK | 24.6 | 27.6 | 29.4 | 26.2 | 30.7 |
| 10 uL PK | 24.6 | 27.9 | 29.9 | 26.7 | 31.0 |
| 20 uL PK | 24.6 | 27.6 | 29.5 | 26.4 | 31.3 |
| 40 uL PK | 24.6 | 27.5 | 29.5 | 25.9 | 30.7 |

| | delta Ct | | |
|---|---|---|---|
| | ESR | PGR | ERBB2 |
| no PK | 0.9 | 2.8 | 2.6 |
| 20 uL PK (80 C., overnight) | 1.2 | 3.0 | 2.3 |
| 5 uL PK | 1.8 | 4.8 | 3.2 |
| 10 uL PK | 2.1 | 5.3 | 3.3 |
| 20 uL PK | 1.9 | 4.9 | 3.1 |
| 40 uL PK | 2.0 | 4.9 | 3.6 |

Experiment D, Varying NaCl Concentration A

TABLE 8

Results -- Effect of NaCl concentration.

| NaCl conc | PGR | ESR | CYFIP1 | ERBB2 | MKi67 |
|---|---|---|---|---|---|
| 200 mM | 25.6 | 22.8 | 29.7 | 26.9 | 31.7 |
| 200 mM | 26.5 | 28.3 | 29.4 | 27.3 | 31.2 |
| 200 mM | 26.6 | 28.3 | 30.1 | 27.6 | 31.7 |
| 200 mM | 26.1 | 26.9 | 29.3 | 26.4 | 31.1 |
| 300 mM | 24.8 | 26.7 | 29.2 | 25.5 | 30.1 |
| 300 mM | 25.6 | 28.1 | 29.8 | 26.7 | 30.8 |
| 300 mM | 25.0 | 27.6 | 29.0 | 26.0 | 30.6 |
| 300 mM | 25.1 | 27.6 | 29.4 | 25.5 | 30.7 |
| 400 mM | 24.6 | 27.4 | 29.5 | 25.7 | 30.7 |
| 400 mM | 24.9 | 26.4 | 27.8 | 25.2 | 30.1 |
| 400 mM | 25.4 | 28.2 | 29.7 | 26.2 | 31.0 |
| 400 mM | 24.5 | 26.9 | 29.4 | 25.5 | 30.8 |

Figure 2A:
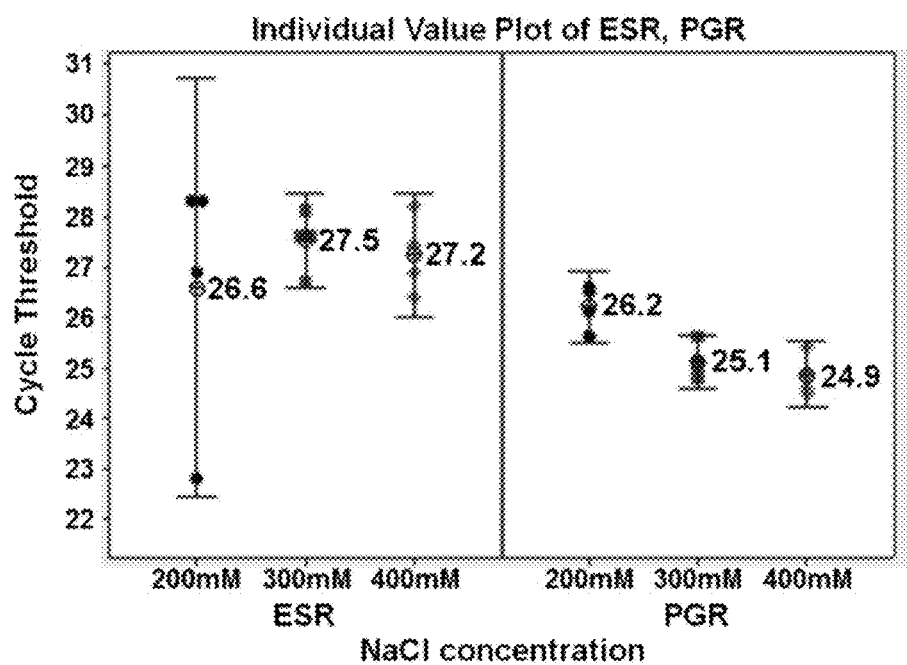
FIGS. 2A-2C illustrate results of varying salinity of the lysis solution.
Figure 2B:
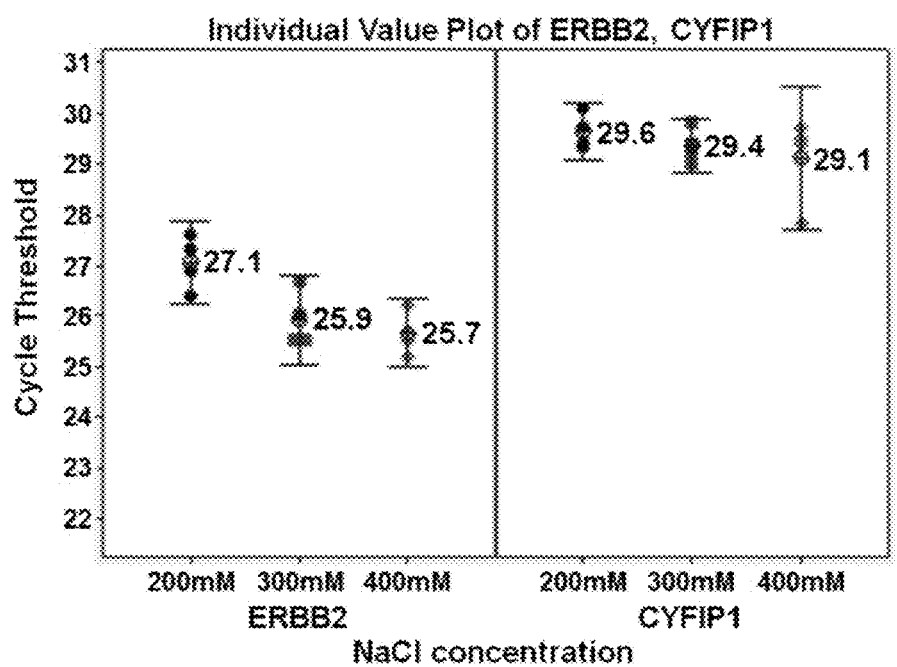
Figure 2C:
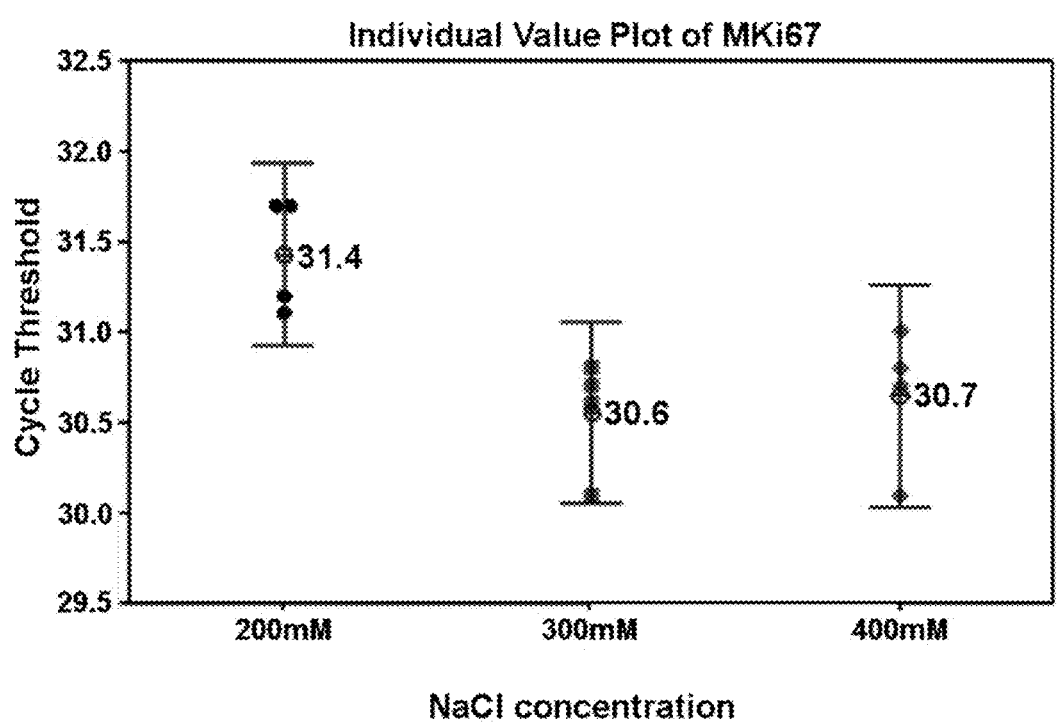

FIG. 2A shows cycle threshold as a function of NaCl concentration for ESR and PGR. FIG. 2B shows cycle threshold as a function of NaCl concentration for ERBB2 and CYFIP1. FIG. 2C shows cycle threshold as a function of NaCl concentration for MKi67.

Experiment E, Varying NaCl Concentration B

Goals: Process BT474 cell button samples with m3FFPE, m3cFFPE, m3dFFPE and m3eFFPE lysis formulations.

Samples: BT474 FFPE cell buttons, cut and stored at 4° C. 4 um thick and applied to glass slides.

Setup:

Each slide was transferred to a labeled 1.5 mL tube.

1.2 mL of each designated lysis reagent was added to its tube.

20 uL of Proteinase K was added to each sample.

The samples were vortexed for 5 seconds, then incubated at 80 C for 30 minutes.

The samples were vortexed for 5 seconds and pulse spun.

Each sample was transferred to a labeled 5 mL vial containing 1.2 mL 100% Ethanol.

The samples were each vortexed for at least 15 seconds.

Cartridge A's, NGB, were prepared with reaction beads in chamber 11 and liquid reagents in chambers 2 and 5.

Four 520 uL aliquots from each sample was transferred to chamber 3 in their designated cartridges.

All carts were run using the 140421 Strat+2X sonicate ADF.

TABLE 9

Results.

| BT474 (N = 4) | cycle threshold | | | | | Cell line status |
|---|---|---|---|---|---|---|
| | PGR | ESR | CYFIP1 | ERBB2 | MKi67 | |
| m3FFPE (200 nM NaCl) | 25.4 | 27.6 | 29.6 | 26.1 | 30.8 | ER: pos, PR: pos, HER2: amplified |
| m3cFFPE (400 nM NaCl) | 24.6 | 27.2 | 28.8 | 25.4 | 29.8 | |
| m3dFFPE (800 nM NaCl) | 25.4 | 27.8 | 29.4 | 26.1 | 31.0 | |
| m3eFFPE (1200 nM NaCl) | 26.1 | 28.3 | 29.9 | 26.6 | 31.5 | |

| | delta Ct | | |
|---|---|---|---|
| | ESR | PGR | ERBB2 |
| m3FFPE (200 nM NaCl) | 2.0 | 4.2 | 3.5 |
| m3cFFPE (400 nM NaCl) | 1.6 | 4.2 | 3.4 |
| m3dFFPE (800 nM NaCl) | 1.6 | 4.1 | 3.4 |
| m3eFFPE (1200 nM NaCl) | 1.5 | 3.7 | 3.2 |

Experiment F, Varying Antifoam Concentrations

Goals: Process BT474 FFPE cell buttons with m3f FFPE lysis reagents with varying antifoam concentrations.

Samples: BT474 FFPE cell buttons. Slides are 4 um thick and applied to glass slides.

Setup:

Each slide was transferred to a labeled 1.5 mL tube.

1.2 mL of each designated lysis reagent was added to its tube.

The samples were vortexed for 5 seconds, then incubated at 80° C. for 30 minutes The samples were vortexed for 5 seconds and pulse spun.

Each sample was transferred to a labeled 5 mL vial containing 1.2 mL 100% Ethanol.

The samples were each vortexed for at least 15 seconds.

Cart A's, NGB, were prepared with reaction beads in chamber 11 and liquid reagents in chambers 2 and 5.

Four 520 uL aliquots per test condition were transferred to chamber 3 in their designated cartridges.

All carts were run using the 140421 Strat+2X sonicate ADF.

TABLE 10

Results:

| Test Condition (N = 4) | cycle threshold | | | | | delta Ct | | |
|---|---|---|---|---|---|---|---|---|
| | PGR | ESR | CYFIP1 | ERBB2 | MKi67 | ESR | PGR | ERBB2 |
| 0.10% antifoam | 25.8 | 27.6 | 30.1 | 27.3 | 32.2 | 2.5 | 4.3 | 2.8 |
| 0.04% antifoam | 25.1 | 27.4 | 29.3 | 26.4 | 31.1 | 1.9 | 4.2 | 2.9 |
| 0.01% antifoam | 25.8 | 27.9 | 29.2 | 26.2 | 31.5 | 1.3 | 3.4 | 2.9 |
| 0.005% antifoam | 25.2 | 27.6 | 29.4 | 26.4 | 31.6 | 1.8 | 4.2 | 3.0 |

Experiment G, Sample Stability Study

Additionally a lysate stability study was performed in which FFPE cell buttons and FPE patient samples were lysed, mixed with Ethanol and then stored at −20 C with scheduled test dates (see, e.g., Table 11, below and FIGS. 3A and 3B).

TABLE 11

Stability study results.

| sample | lysis | day | PGR | ESR | CYFIP1 | ERBB2 | MKi67 |
|---|---|---|---|---|---|---|---|
| 015465T2 | m3f | 0 | 26.9 | 20.3 | 26.0 | 24.7 | 25.4 |
| 015465T2 | m3f | 7 | 26.6 | 20.3 | 26.6 | 25.5 | 25.5 |
| 015465T2 | m3f | 15 | 27.2 | 20.7 | 26.6 | 24.6 | 25.1 |
| 015465T2 | m3f | 28 | 27.3 | 20.8 | 26.4 | 24.0 | 26.3 |
| 015465T2 | m3f | 35 | 27.3 | 21.1 | 26.9 | 25.4 | 26.4 |
| 015465T2 | m3f | 62 | 27.7 | 21.4 | 27.2 | 24.8 | 27.0 |
| BT474 | m3f | 0 | 25.8 | 28.2 | 29.7 | 26.5 | 31.4 |
| BT474 | m3f | 7 | 25.5 | 27.6 | 29.4 | 26.4 | 31.4 |
| BT474 | m3f | 15 | 25.6 | 27.6 | 29.1 | 26.2 | 31.4 |
| BT474 | m3f | 28 | 25.7 | 28.1 | 29.7 | 27.2 | 31.3 |
| BT474 | m3f | 35 | 25.5 | 28.3 | 29.7 | 26.2 | 31.3 |
| BT474 | m3f | 62 | 25.9 | 28.2 | 29.2 | 26.6 | 32.7 |
| RA00-0741 | m3f | 0 | 35.1 | 21.9 | 25.7 | 24.0 | 25.7 |
| RA00-0741 | m3f | 7 | 34.8 | 22.2 | 25.7 | 23.8 | 25.8 |
| RA00-0741 | m3f | 15 | 37.8 | 22.1 | 25.9 | 23.6 | 25.6 |
| RA00-0741 | m3f | 28 | 40.7 | 22.1 | 25.8 | 23.6 | 26.6 |
| RA00-0741 | m3f | 35 | 35.9 | 21.6 | 25.3 | 23.3 | 25.6 |
| RA00-0741 | m3f | 62 | 45.0 | 21.7 | 25.3 | 22.8 | 26.1 |
| 015465T2 | m5 | 0 | 27.9 | 20.6 | 26.5 | 24.5 | 24.7 |
| 015465T2 | m5 | 7 | 27.1 | 21.1 | 26.4 | 24.6 | 25.8 |
| 015465T2 | m5 | 15 | 28.9 | 22.9 | 27.5 | 26.3 | 27.5 |
| 015465T2 | m5 | 28 | 28.5 | 21.7 | 27.3 | 26.3 | 26.5 |
| 015465T2 | m5 | 35 | 29.1 | 22.8 | 28.6 | 27.1 | 27.6 |
| 015465T2 | m5 | 62 | 29.6 | 21.3 | 28.4 | 27.3 | 27.1 |
| BT474 | m5 | 0 | 25.6 | 28.5 | 29.7 | 26.5 | 32.1 |
| BT474 | m5 | 7 | 25.9 | 28.2 | 29.6 | 26.6 | 32.3 |
| BT474 | m5 | 15 | 25.4 | 19.8 | 29.5 | 26.6 | 31.6 |
| BT474 | m5 | 28 | 25.7 | 27.9 | 29.2 | 26.5 | 30.8 |
| BT474 | m5 | 35 | 26.2 | 29.1 | 29.5 | 27.6 | 31.7 |
| BT474 | m5 | 62 | 26.2 | 28.5 | 29.6 | 27.3 | 31.5 |
| RA00-0741 | m5 | 0 | 34.7 | 23.5 | 26.9 | 25.1 | 27.1 |
| RA00-0741 | m5 | 7 | 35.1 | 22.5 | 25.9 | 24.8 | 25.9 |
| RA00-0741 | m5 | 15 | 37.9 | 21.7 | 26.0 | 24.2 | 25.5 |
| RA00-0741 | m5 | 28 | 37.1 | 22.2 | 25.7 | 24.9 | 26.0 |
| RA00-0741 | m5 | 35 | 36.7 | 22.2 | 26.1 | 24.6 | 25.4 |

TABLE 11-continued

Stability study results.

| sample | lysis | day | PGR | ESR | CYFIP1 | ERBB2 | MKi67 |
|---|---|---|---|---|---|---|---|
| RA00-0741 | m5 | 62 | 37.4 | 23.2 | 26.4 | 25.2 | 25.9 |

FIG. 3A shows the stability (repeatable of cycle threshold) for ESR, and PGR for samples stored over 62 days. FIG. 3B shows the stability (repeatable of cycle threshold) for ESR, and PGR for samples stored over 62 days.

Experiment H, Analysis of Tissue Microarray

Goal: Test the cores from slide 1, (TMA30 block from Yale), in the Stratifier assay.
Test Samples: 30 cores on a single slide, TMA block from Yale. Slide YTMA 308-1, Breast ER, 1-29-15, slide 1. Slide was cut 4 um thick.

TABLE 12

Results:

| | Cycle Threshold | | | | |
|---|---|---|---|---|---|
| Sample ID | CYFIP | PGR | ESR | ERBB2 | MKi67 |
| TMA30, slide 1, A1 | 27.3 | 45.0 | 23.4 | 29.4 | 27.7 |
| TMA30, slide 1, A2 | 30.2 | 37.0 | 28.8 | 33.9 | 30.7 |
| TMA30, slide 1, A3 | 28.5 | 42.3 | 24.3 | 31.7 | 30.4 |
| TMA30, slide 1, A4 | 27.6 | 37.5 | 31.8 | 30.5 | 28.3 |
| TMA30, slide 1, A6 | 30.3 | 45.0 | 45.0 | 33.1 | 29.6 |
| TMA30, slide 1, B1 | 28.4 | 44.8 | 24.4 | 31.5 | 30.0 |
| TMA30, slide 1, B2 | 30.3 | 37.5 | 31.6 | 36.1 | 34.5 |
| TMA30, slide 1, B3 | 30.5 | 32.4 | 25.6 | 33.2 | 39.4 |
| TMA30, slide 1, B4 | 28.1 | 45.0 | 24.2 | 28.1 | 30.1 |
| TMA30, slide 1, B5 | 30.3 | 45.0 | 45.0 | 31.9 | 30.9 |
| TMA30, slide 1, B6 | 28.3 | 32.4 | 28.7 | 30.4 | 30.7 |
| TMA30, slide 1, C1 | 30.1 | 35.5 | 25.2 | 32.3 | 36.1 |
| TMA30, slide 1, C2 | 31.1 | 33.2 | 25.1 | 32.9 | 33.4 |
| TMA30, slide 1, C3 | 28.3 | 41.3 | 30.2 | 31.2 | 29.2 |
| TMA30, slide 1, C4 | 30.3 | 40.0 | 31.2 | 34.2 | 32.6 |
| TMA30, slide 1, C5 | 33.0 | 35.0 | 29.4 | 37.5 | 45.0 |
| TMA30, slide 1, C6 | 28.3 | 28.6 | 23.4 | 31.2 | 31.4 |
| TMA30, slide 1, D1 | 30.3 | 45.0 | 33.2 | 38.3 | 29.9 |
| TMA30, slide 1, D2 | 29.4 | 28.8 | 24.1 | 31.0 | 43.4 |
| TMA30, slide 1, D3 | 27.2 | 28.7 | 25.3 | 32.2 | 36.8 |
| TMA30, slide 1, D4 | 29.9 | 37.8 | 26.2 | 31.9 | 36.2 |
| TMA30, slide 1, D5 | 28.3 | 45.0 | 30.2 | 31.8 | 27.1 |
| TMA30, slide 1, D6 | 31.8 | 45.0 | 32.1 | 36.5 | 39.5 |
| TMA30, slide 1, E1 | 29.0 | 38.4 | 26.8 | 31.4 | 30.4 |
| TMA30, slide 1, E2 | 27.2 | 45.0 | 32.1 | 32.7 | 27.6 |
| TMA30, slide 1, E3 | 28.0 | 38.4 | 45.0 | 28.1 | 28.3 |
| TMA30, slide 1, E4 | 29.8 | 45.0 | 24.4 | 32.2 | 45.0 |
| TMA30, slide 1, E5 | 28.1 | 45.0 | 33.9 | 40.0 | 31.9 |
| TMA30, slide 1, E6 | 29.7 | 44.2 | 31.9 | 37.1 | 30.5 |
| TMA30, slide 1, E7 | 29.7 | 45.0 | 31.7 | 36.1 | 36.7 |

TABLE 13

Results:

| | Delta Ct | | | |
|---|---|---|---|---|
| Sample ID | MKi67(−5) | ESR(−1) | PGR(−4) | ERBB2(0) |
| TMA30, slide 1, A1 | −0.4 | 3.9 | −17.7 | −2.1 |
| TMA30, slide 1, A2 | −0.5 | 1.4 | −6.8 | −3.7 |
| TMA30, slide 1, A3 | −1.9 | 4.2 | −13.8 | −3.2 |
| TMA30, slide 1, A4 | −0.7 | −4.2 | −9.9 | −2.9 |
| TMA30, slide 1, A6 | 0.7 | −14.7 | −14.7 | −2.8 |
| TMA30, slide 1, B1 | −1.6 | 4.0 | −16.4 | −3.1 |
| TMA30, slide 1, B2 | −4.2 | −1.3 | −7.2 | −5.8 |
| TMA30, slide 1, B3 | −8.9 | 4.9 | −1.9 | −2.7 |
| TMA30, slide 1, B4 | −2.0 | 3.9 | −16.9 | 0.0 |
| TMA30, slide 1, B5 | −0.6 | −14.7 | −14.7 | −1.6 |
| TMA30, slide 1, B6 | −2.4 | −0.4 | −4.1 | −2.1 |
| TMA30, slide 1, C1 | −6.0 | 4.9 | −5.4 | −2.2 |
| TMA30, slide 1, C2 | −2.3 | 6.0 | −2.1 | −1.8 |
| TMA30, slide 1, C3 | −0.9 | −1.9 | −13.0 | −2.9 |
| TMA30, slide 1, C4 | −2.3 | −0.9 | −9.7 | −3.9 |
| TMA30, slide 1, C5 | −12.0 | 3.6 | −2.0 | −4.5 |
| TMA30, slide 1, C6 | −3.1 | 4.9 | −0.3 | −2.9 |
| TMA30, slide 1, D1 | 0.4 | −2.9 | −14.7 | −8.0 |
| TMA30, slide 1, D2 | −14.0 | 5.3 | 0.6 | −1.6 |
| TMA30, slide 1, D3 | −9.6 | 1.9 | −1.5 | −5.0 |
| TMA30, slide 1, D4 | −6.3 | 3.7 | −7.9 | −2.0 |
| TMA30, slide 1, D5 | 1.2 | −1.9 | −16.7 | −3.5 |
| TMA30, slide 1, D6 | −7.7 | −0.3 | −13.2 | −4.7 |
| TMA30, slide 1, E1 | −1.4 | 2.2 | −9.4 | −2.4 |
| TMA30, slide 1, E2 | −0.4 | −4.9 | −17.8 | −5.5 |
| TMA30, slide 1, E3 | −0.3 | −17.0 | −10.4 | −0.1 |
| TMA30, slide 1, E4 | −15.2 | 5.4 | −15.2 | −2.4 |
| TMA30, slide 1, E5 | −3.8 | −5.8 | −16.9 | −11.9 |
| TMA30, slide 1, E6 | −0.8 | −2.2 | −14.5 | −7.4 |
| TMA30, slide 1, E7 | −7.0 | −2.0 | −15.3 | −6.4 |

TABLE 14

Results:

| | potential Stratifier call | | | |
|---|---|---|---|---|
| sample ID | MKi67 | ER | PR | HER2 |
| TMA30, slide 1, A1 | pos | pos | neg | neg |
| TMA30, slide 1, A2 | pos | pos | neg | neg |
| TMA30, slide 1, A3 | pos | pos | neg | neg |
| TMA30, slide 1, A4 | pos | neg | neg | neg |
| TMA30, slide 1, A6 | pos | neg | neg | neg |
| TMA30, slide 1, B1 | pos | pos | neg | neg |
| TMA30, slide 1, B2 | pos | neg | neg | neg |
| TMA30, slide 1, B3 | low | pos | pos | neg |
| TMA30, slide 1, B4 | pos | pos | neg | pos |
| TMA30, slide 1, B5 | pos | neg | neg | neg |
| TMA30, slide 1, B6 | pos | pos | neg | neg |
| TMA30, slide 1, C1 | low | pos | neg | neg |
| TMA30, slide 1, C2 | pos | pos | pos | neg |
| TMA30, slide 1, C3 | pos | neg | neg | neg |
| TMA30, slide 1, C4 | pos | neg | neg | neg |
| TMA30, slide 1, C5 | low | pos | pos | neg |
| TMA30, slide 1, C6 | pos | pos | pos | neg |
| TMA30, slide 1, D1 | pos | neg | neg | neg |
| TMA30, slide 1, D2 | low | pos | pos | neg |
| TMA30, slide 1, D3 | low | pos | pos | neg |
| TMA30, slide 1, D4 | low | pos | neg | neg |
| TMA30, slide 1, D5 | pos | neg | neg | neg |
| TMA30, slide 1, D6 | low | pos | neg | neg |
| TMA30, slide 1, E1 | pos | pos | neg | neg |
| TMA30, slide 1, E2 | pos | neg | neg | neg |
| TMA30, slide 1, E3 | pos | neg | neg | neg |
| TMA30, slide 1, E4 | low | pos | neg | neg |
| TMA30, slide 1, E5 | pos | neg | neg | neg |
| TMA30, slide 1, E6 | pos | neg | neg | neg |
| TMA30, slide 1, E7 | low | neg | neg | neg |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A lysis solution for the extraction of a nucleic acid from a cell or tissue sample, said lysis solution comprising:
   NaCl at a concentration of greater than about 300 mM;
   a buffer sufficient to maintain the pH of said solution at a pH ranging from about pH 6.8 to about pH 7.3;
   a chelating agent;
   $MgCl_2$ at a concentration of at least 2 mM, but less than about 50 mM; and
   a detergent.

2. The lysis solution of claim 1, wherein said solution comprises:
   an antifoaming agent; and/or
   a preservative/biocide.

3. The lysis solution of claim 1, wherein said buffer is a HEPES sodium salt buffer.

4. The lysis solution of claim 1, wherein:
   the concentration of said buffer ranges from about 10 mM up to about 100 mM, or from about 20 mM up to about 50 mM, or is about 50 mM; and/or
   the pH of said solution ranges from about 6.8 to about 7.2; and/or
   said NaCl is at a concentration ranging from about 300 mM to about 500 mM, or from about 350 mM up to about 450 mM, or is about 400 mM.

5. The lysis solution of claim 1, wherein said chelating agent comprises an agent selected from the group consisting of N-acetyl-L-cysteine, ethylenediaminetetraacetic acid (EDTA), diethylene triamine pentaacetic acid (DTPA), ethylenediamine-N,N'-disuccinic acid (EDDS), 1,2-bis(o-aminophenoxy)ethane-N,N,N',N'-tetraacetic acid (BAPTA), and a phosphonate chelating agent.

6. The lysis solution of claim 1, wherein:
   the concentration of said chelating agent in said solution ranges from about 5 mM to about 100 mM, or from about 10 mM to about 50 mM, or is about 25 mM; and/or
   the concentration of said $MgCl_2$ ranges from about 2 mM up to about 20 mM, or from about 5 mM up to about 15 mM, or is about 10 mM; and/or
   said detergent comprises about 0.1% to about 2% of said solution, or about 0.5% to about 1.5% of said solution, or about 1% of said solution['].

7. The lysis solution of claim 1, wherein said detergent is an ionic detergent or a non-ionic detergent.

8. The lysis solution of claim 2, wherein said antifoaming agent comprises an organic antifoam emulsion or a siloxane-based antifoam emulsion.

9. The lysis solution of claim 2, wherein said biocide comprises one or more agents selected from the group consisting of sodium azide, sodium dehydroacetate, sodium borate decahydrate, and disodium edetate.

10. The lysis solution of claim 1, wherein said solution comprises:
    about 400 mM NaCl;
    about 50 mM HEPES sodium salt (MW 260.29);
    about 25 mM EDTA;
    about 10 mM $MgCl_2$; and
    about 1% Tween 20.

11. The lysis solution of claim 10, wherein the pH of said solution ranges from about 6.90 to about 7.25.

12. The lysis solution of claim 1, wherein said solution further comprises a protease.

13. A method for extracting a nucleic acid from a cell or tissue sample, said method comprising:
    incubating one or more cell or tissue samples in a lysis solution of claim 1, wherein said incubating is at a temperature ranging from about 50° C. to about 100° C. and said incubation is for a time ranging from about 10 minutes up to about 24 hours to produce one or more lysed samples in which the nucleic acid has been extracted from the one or more cell or tissue samples.

14. The method of claim 13, wherein:
    said temperature is from about 60° C. to about 90° C., or from about 70° C. to about 90° C., or from about 75° C. to about 85° C., or about 80° C.; and/or
    said incubating is for a time ranging from about 15 minutes up to about 12 hours, or from about 20 minutes up to about 8 hours, or from about 30 minutes up to about 6 hours, or from about 30 minutes up to about 4 hours, or from about 30 minutes up to about 2 hours, or for about 15 min, or for about 30 min, or for about 45 min, or for about 60 min, or for about 90 min, or for about 120 min.

15. The method of claim 13, wherein said method further comprises recovering said nucleic acid from said lysis solution.

16. The method of claim 13, wherein said cell or tissue sample(s) are selected from the group consisting of a tissue biopsy, an aspirate, a cell smear, a wipe, a scrape, an archived sample, a fixed tissue section, a formalin-fixed paraffin-embedded section, a cryosection, a cell button, and a tissue microarray.

17. The method of claim 13, wherein:
    said method does not include further steps of deparaffinization and/or additional reagents for deparaffinization; and/or
    said method does not utilize an organic solvent for deparaffinization; and/or
    said incubating is not in the presence of an organic solvent.

18. The method of claim 13, wherein the lysed tissue sample is mixed with a lower alcohol and stored.

19. The method of claim 18, wherein nucleic acids in the lysis solution are stable when the lysis solution is stored over a period of at least 6 hours, or over a period of at least one day, or over a period of at least two days, or over a period of at least 4 days, or over a period of at least one week, or over a period of at least two weeks, or over a period of at least one month, or over a period of at least two months, or over a period of at least three months, or over a period of at least 6 months, or over a period of at least one year, or over a period of at least two years, or over a period of at least 5 years, as measured by post-storage RT-PCR.

20. The method of claim 13, wherein nucleic acids are amplified from the lysed samples at two or more different times.

21. The method of claim 20, wherein said two or more different times are over a period at least 6 hours, or over a period of at least one day, or over a period of at least two days, or over a period of at least 4 days, or over a period of at least one week, or over a period of at least two weeks, or over a period of at least one month, or over a period of at least two months, or over a period of at least three months, or over a period of at least 6 months, or over a period of at least one year, or over a period of at least two years, or over a period of at least 5 years.

22. A method for quantitative measurement of gene expression of a target gene in a formalin-fixed paraffin-embedded tissue sample comprising:

extracting an RNA from a formalin-fixed paraffin-embedded biological tissue sample according to the method of claim 13;

subjecting the extracted nucleic acid to amplification using a pair of oligonucleotide primers capable of amplifying a region of a target gene mRNA, to obtain an amplified sample; and determining the presence and/or quantity of said target gene mRNA.

23. A kit for the extraction of a nucleic acid from a cell and/or tissue sample, said kit comprising a container containing a lysis solution of claim 1.

24. The lysis solution of claim 1, wherein said solution comprises:

400 mM NaCl;
50 mM HEPES sodium salt (MW 260.29);
25 mM EDTA;
10 mM $MgCl_2$; and
1% Tween 20.

25. The lysis solution of claim 24, wherein the pH of said solution ranges from about 6.90 to about 7.25.

26. The lysis solution of claim 25, wherein said solution further comprises a protease.

27. A method for extracting a nucleic acid from a cell or tissue sample, said method comprising:

incubating one or more cell or tissue samples in a lysis solution of claim 26, wherein said incubating is at a temperature ranging from about 50° C. to about 100° C. and said incubation is for a time ranging from about 10 minutes up to about 24 hours to produce one or more lysed samples in which the nucleic acid has been extracted from the one or more cell or tissue samples.

28. The method of claim 27, wherein:

said method does not include further steps of deparaffinization and/or additional reagents for deparaffinization; and/or said method does not utilize an organic solvent for deparaffinization; and/or said incubating is not in the presence of an organic solvent.

* * * * *